US009833136B2

(12) United States Patent
Bagherinia

(10) Patent No.: US 9,833,136 B2
(45) Date of Patent: Dec. 5, 2017

(54) SYSTEMS AND METHODS FOR OCULAR ANTERIOR SEGMENT TRACKING, ALIGNMENT, AND DEWARPING USING OPTICAL COHERENCE TOMOGRAPHY

(71) Applicants: CARL ZEISS MEDITEC, INC., Dublin, CA (US); CARL ZEISS MEDITEC AG, Jena (DE)

(72) Inventor: Homayoun Bagherinia, Oakland, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 0 days.

(21) Appl. No.: 15/104,447

(22) PCT Filed: Dec. 18, 2014

(86) PCT No.: PCT/EP2014/078458
§ 371 (c)(1),
(2) Date: Jun. 14, 2016

(87) PCT Pub. No.: WO2015/091796
PCT Pub. Date: Jun. 25, 2015

(65) Prior Publication Data
US 2016/0317012 A1 Nov. 3, 2016

Related U.S. Application Data

(60) Provisional application No. 61/918,107, filed on Dec. 19, 2013, provisional application No. 62/064,932, filed on Oct. 16, 2014.

(51) Int. Cl.
A61B 3/14 (2006.01)
A61B 3/00 (2006.01)
(Continued)

(52) U.S. Cl.
CPC ............ *A61B 3/0025* (2013.01); *A61B 3/102* (2013.01); *A61B 3/107* (2013.01); *A61B 3/117* (2013.01);
(Continued)

(58) Field of Classification Search
USPC .................................................. 351/200-246
See application file for complete search history.

(56) References Cited

U.S. PATENT DOCUMENTS 7,884,945 B2    2/2011   Srinivasan et al.
8,414,564 B2    4/2013   Goldshleger et al.
(Continued)

FOREIGN PATENT DOCUMENTS

WO    2010/129544 A1    11/2010
WO    2014/021782 A1    2/2014

OTHER PUBLICATIONS

Baumann et al., "Full Range Complex Spectral Domain Optical Coherence Tomography without Additional Phase Shifters", Optics Express, vol. 15, No. 20, Oct. 1, 2007, pp. 13375-13387.
(Continued)

*Primary Examiner* — Mohammed Hasan
(74) *Attorney, Agent, or Firm* — Morrison & Foerster LLP

(57) ABSTRACT

The present application discloses methods and systems to track the anterior segment while establishing a position of the delay which will permit good control of the placement of anterior segment structures. This allows accurate dewarping by maximizing the amount of corneal surface that is imaged as well as reducing or eliminating overlap between real and complex conjugate images present in frequency-domain optical coherence tomography. A method to dewarp surfaces given partial corneal surface information is also disclosed.

23 Claims, 22 Drawing Sheets

(51) Int. Cl.

| | |
|---|---|
| *G06T 3/00* | (2006.01) |
| *G06T 5/00* | (2006.01) |
| *G06T 7/00* | (2017.01) |
| *A61B 3/10* | (2006.01) |
| *A61B 3/107* | (2006.01) |
| *A61B 3/117* | (2006.01) |
| *G06K 9/00* | (2006.01) |
| *G06K 9/52* | (2006.01) |
| *G06T 7/60* | (2017.01) |
| *G06T 7/70* | (2017.01) |

(52) U.S. Cl.
CPC ....... *G06K 9/0061* (2013.01); *G06K 9/00617* (2013.01); *G06K 9/52* (2013.01); *G06T 3/0093* (2013.01); *G06T 5/006* (2013.01); *G06T 7/0012* (2013.01); *G06T 7/60* (2013.01); *G06T 7/70* (2017.01); *G06T 2207/10072* (2013.01); *G06T 2207/10101* (2013.01); *G06T 2207/30041* (2013.01); *G06T 2207/30196* (2013.01)

(56) References Cited

U.S. PATENT DOCUMENTS

| | | | |
|---|---|---|---|
| 8,605,287 | B2 | 12/2013 | Ko et al. |
| 2008/0100612 | A1 | 5/2008 | Dastmalchi et al. |
| 2012/0188555 | A1 | 7/2012 | Izatt et al. |
| 2012/0249956 | A1 | 10/2012 | Narasimha-Iyer et al. |
| 2012/0271288 | A1* | 10/2012 | Marziliano ............... G06T 7/75 606/6 |
| 2013/0188140 | A1 | 7/2013 | Bagherinia et al. |
| 2013/0208240 | A1* | 8/2013 | Sharma .................. A61B 3/102 351/206 |

OTHER PUBLICATIONS

Canny, John, "A Computational Approach to Edge Detection", IEEE Transactions on Pattern Analysis and Machine Intelligence, vol. PAMI-8, No. 6, Nov. 1986, pp. 679-698.
Fischler et al., "Random Sample Consensus: A Paradigm for Model Fitting with Applications to Image Analysis and Automated Cartography", Communications of the ACM, vol. 24, No. 6, Jun. 1981, pp. 381-395.
Forbes, G. W., "Shape Specification for Axially Symmetric Optical Surfaces", Optics Express, vol. 15, No. 8, Apr. 16, 2007, pp. 5218-5226.
Friedman et al., "Anterior Chamber Angle Assessment Techniques", Survey of Ophthalmology, vol. 53, No. 3, May-Jun. 2008, pp. 250-273.
Hofer et al., "Fast Dispersion Encoded Full Range Optical Coherence Tomography for Retinal Imaging at 800 nm and 1060 nm", Optics Express, vol. 18, No. 5, Mar. 1, 2010, pp. 4898-4919.
International Preliminary Report on Patentability received for PCT Patent Application No. PCT/EP2014/078458, dated Jun. 30, 2016, 12 pages.
International Search Report and Written Opinion received for PCT Patent Application No. PCT/EP2014/078458, dated Jul. 2, 2015, 17 pages.
Ishikawa et al., "Anterior Segment Imaging: Ultrasound Biomicroscopy", Ophthalmology Clinics of North America, vol. 17, No. 1, Mar. 2004, pp. 7-20.
Kovesi, Peter, "Phase Congruency Detects Corners and Edges", Proc. VIIth Digital Image Computing: Techniques and Applications, School of Computer Science & Software Engineering, Dec. 10-12, 2003, 10 pages.
Leung et al., "Anterior Chamber Angle Measurement with Anterior Segment Optical Coherence Tomography: A Comparison between Slit Lamp OCT and Visante OCT", Investigative Ophthalmology & Visual Science, vol. 49, No. 8, Aug. 2008, pp. 3469-3474.
Makita et al., "Optical Coherence Angiography", Optics Express, vol. 14, No. 17, Aug. 21, 2006, pp. 7821-7840.
Maurer et al., "A Linear Time Algorithm for Computing Exact Euclidean Distance Transforms of Binary Images in Arbitrary Dimensions", IEEE Transactions on Pattern Analysis and Machine Intelligence, vol. 25, No. 2, Feb. 2003, pp. 265-270.
Meyer, Fernand, "Topographic Distance and Watershed Lines", Signal Processing, vol. 38, 1994, pp. 113-125.
Narayanaswamy et al., "Comparison of Ocular Response Analyzer Parameters in Chinese Subjects With Primary Angle-Closure and Primary Open-Angle Glaucoma", Arch Ophthalmol, vol. 129, No. 4, Apr. 2011, pp. 429-434.
Nongpiur et al., "Novel Association of Smaller Anterior Chamber Width with Angle Closure in Singaporeans", Ophthalmology, vol. 117, No. 10, Oct. 2010, pp. 1967-1973.
Ortiz et al., "Optical Coherence Tomography for Quantitative Surface Topography", Applied Optics, vol. 48, No. 35, Dec. 10, 2009, pp. 6708-6715.
Ortiz et al., "Optical Distortion Correction in Optical Coherence Tomography for Quantitative Ocular Anterior Segment by Three-Dimensional Imaging", Optics Express, vol. 18, No. 3, Feb. 1, 2010, pp. 2782-2796.
Paglieroni, D. W., "Distance Transforms: Properties and Machine Vision Applications", CVGIP: Graphical Models and Image Processing, vol. 54, No. 1, Jan. 1992, pp. 56-74.
Parker, J. R., "Algorithms for Image Processing and Computer Vision", 2nd Edition, Chapter 4, Grey-Level Segmentation, Wiley Publishing Inc., 2010, pp. 137-175.
Perera et al., "Imaging of the Iridocorneal Angle with the RTVue Spectral Domain Optical Coherence Tomography", Investigative Ophthalmology & Visual Science, vol. 53, No. 4, Apr. 2012, pp. 1710-1713.
Quigley et al., "Iris Cross-Sectional Area Decreases With Pupil Dilation and its Dynamic Behavior is a Risk Factor in Angle Closure", J. Glaucoma, vol. 18, No. 3, Mar. 2009, pp. 173-179.
Quigley, Harry A., "Angle-Closure Glaucoma—Simpler Answers to Complex Mechanisms: LXVI Edward Jackson Memorial Lecture", American Journal of Ophthalmology, vol. 148, No. 5, Nov. 2009, pp. 657-669.
Radhakrishnan et al., "Development in Anterior Segment Imaging for Glaucoma", Current Opinion in Ophthalmology, vol. 25, No. 2, Mar. 2014, pp. 98-103.
Radhakrishnan et al., "Reproducibility of Anterior Chamber Angle Measurements Obtained with Anterior Segment Optical Coherence Tomography", Investigative Ophthalmology & Visual Science, vol. 48, No. 8, Aug. 2007, pp. 3683-3688.
Rosenfeld et al., "Sequential Operations in Digital Picture Processing", Journal of the Association for Computing Machinery, vol. 13, No. 4, Oct. 1966, pp. 471-494.
Smith, Redmond J. H., "A New Method of Estimating the Depth of the Anterior Chamber", British Journal of Ophthalmology, vol. 63, 1979, pp. 215-220.
Spaide et al., "Enhanced Depth Imaging Spectral-Domain Optical Coherence Tomography", American Journal of Ophthalmology, vol. 146, No. 4, Oct. 2008, pp. 496-500.
Wang, Ruikang K., "In Vivo Full Range Complex Fourier Domain Optical Coherence Tomography", Applied Physics Letters, vol. 90, 2007, pp. 054103-1-054103-3.
Westphal et al., "Correction of Geometric and Refractive Image Distortions in Optical Coherence Tomography Applying Fermat's Principle", Optics Express, vol. 10, No. 9, May 6, 2002, pp. 397-404.
Wirbelauer et al., "Noncontact Goniometry With Optical Coherence Tomography", Archives of Ophthalmology, vol. 123, Feb. 2005, pp. 179-185.
Wojtkowski et al., "Full Range Complex Spectral Optical Coherence Tomography Technique in Eye Imaging", Optics Letters, vol. 27, No. 16, Aug. 15, 2002, pp. 1415-1417.
Wu et al., "Association of Narrow Angles With Anterior Chamber Area and Volume Measured With Anterior-Segment Optical Coherence Tomography", Arch Ophthalmol, vol. 129, No. 5, May 2011, pp. 569-574.

(56) References Cited

OTHER PUBLICATIONS

Zhang et al., "Full Range Polarization-Sensitive Fourier Domain Optical Coherence Tomography", Optics Express, vol. 12, No. 24, Nov. 29, 2004, pp. 6033-6039.

Zhang et al., "Removal of a Mirror Image and Enhancement of the Signal-to-Noise Ratio in Fourier-Domain Optical Coherence Tomography using an Electro-Optic Phase Modulator", Optics Letters, vol. 30, No. 2, Jan. 15, 2005, pp. 147-149.

\* cited by examiner

FIG 1(a)
FIG 1(b)
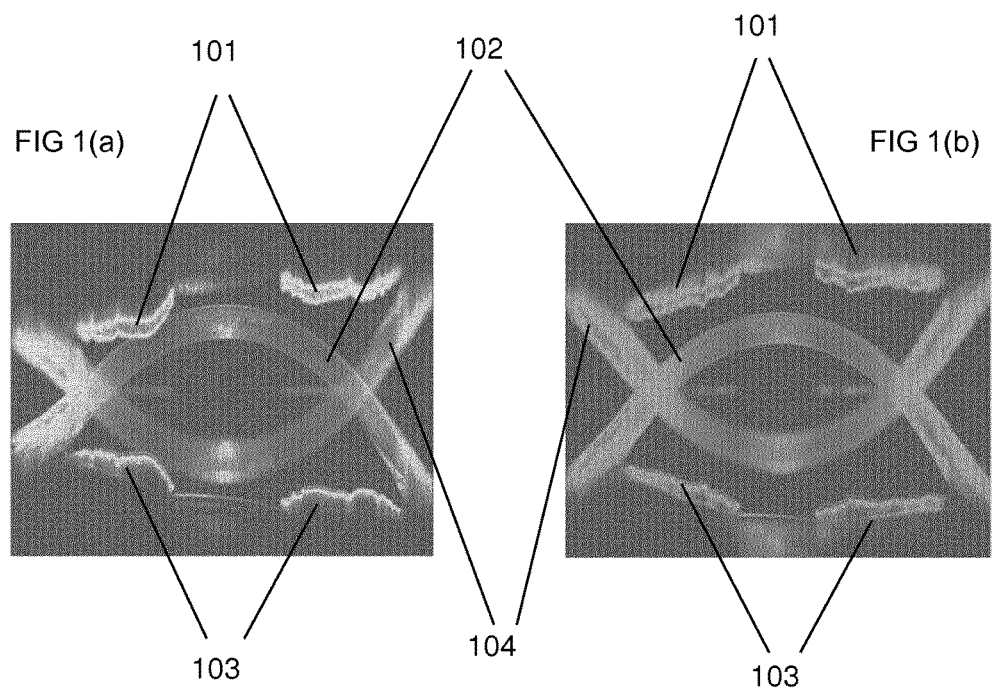
FIG. 2
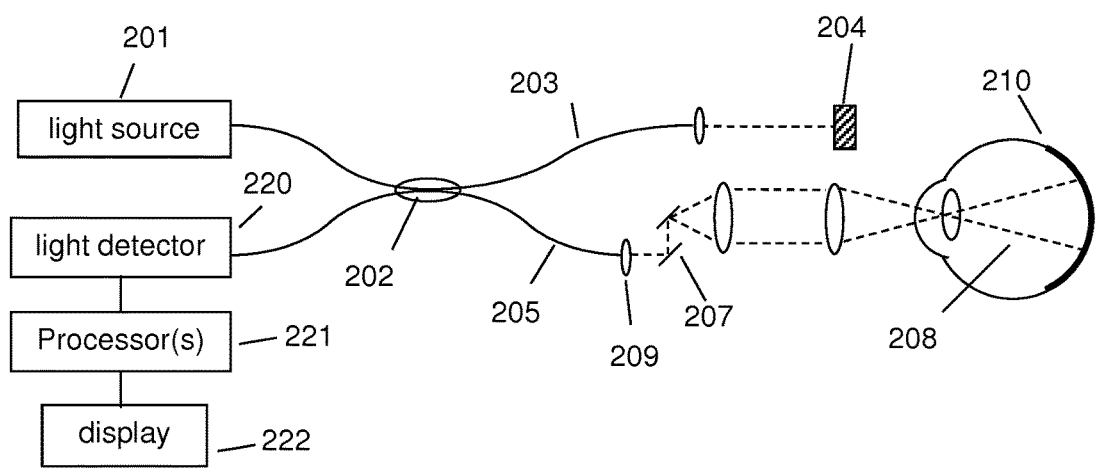

1104

SYSTEMS AND METHODS FOR OCULAR ANTERIOR SEGMENT TRACKING, ALIGNMENT, AND DEWARPING USING OPTICAL COHERENCE TOMOGRAPHY

CROSS REFERENCE TO RELATED APPLICATIONS

This application is a National Phase application under 35 U.S.C. §371 of International Application No. PCT/EP2014/078458, filed Dec. 18, 2014, which claims priority from provisional applications U.S. Ser. No. 61/918,107, filed Dec. 19, 2013 and U.S. Ser. No. 62/064,932, filed Oct. 10, 2014, the disclosures of each of which are herein incorporated by reference in their entirety.

TECHNICAL FIELD

The present application discloses methods and systems in optical coherence tomography to improve the quality of anterior segment imaging in the eye of a patient.

BACKGROUND

Optical coherence tomography (OCT) is an optical imaging technology for imaging non-invasively biological tissues. The basis of the technique is low-coherence interference between a reference beam and light reflected from structural surfaces such as tissues. Depending on the scanning or imaging configuration, various dimensions can be probed such as a line (called an A-scan), transverse scanning can produce a 2D surface known as a B-scan, and with multiple adjacent surfaces a 3D volume can be obtained.

In frequency-domain OCT (FD-OCT), the optical path length difference between the sample and reference arm is not mechanically scanned as it is in time-domain OCT (TD-OCT). A full A-scan can be obtained in parallel for all points along the sample axial line within a short time, typically determined by the wavelength sweep rate of a swept source in swept-source OCT (SS-OCT) or the line scan rate of the line scan camera in spectral-domain OCT (SD-OCT).

The spectral interferogram acquired through FD-OCT encodes the longitudinal sample structure at the focal spot. To recover the sample structure, the interference pattern can be inverse Fourier transformed. This transform yields three components: a DC component, a cross-correlation component, and an auto-correlation component. The DC terms are often the largest component and are pathlength-independent. The cross-correlation terms contain the information of interest—the sample reflectivity profile. The auto-correlation terms represent interference between the different reflectors within the sample. Elements of all three of these components can lead to artifacts that can cause problems in data interpretation or processing.

Imaging of the anterior segment of an eye of a patient using OCT systems presents different problems than encountered with the more commonly performed OCT imaging of the retina. Structures in the anterior segment include the cornea, the iris, the crystalline lens, and other anatomical areas as well. Problems encountered with OCT anterior segment imaging include distortions of the acquired image from a true geometric image, the restricted nature of the depth and breadth of imaging, and the difficulty in obtaining good real-time positional control during image acquisition.

Dewarping

Dewarping is the restoration of the true shape of the cornea and environs due to physical phenomena: the effects of beam geometry distortions and distortions due to the bending of light by various refractive surfaces. These problems can be eliminated by dewarping algorithms (Westphal et al. 2002; Ortiz et al. 2009, 2010). Accurate dewarping is required for an accurate analysis of anterior segment OCT image data to characterize pathologies (such as keratoconus) or metrics of pathologies (geometric metrics or measurements of structures contained therein).

Beam geometry distortions arise due to the non-telecentric scanning of the OCT beam used to obtain a 2D image (a B-scan) and also due to the optical path length, which is related to scan sag, changing the curvature of the cornea. The beam itself encounters different angles as it scans across, as the cornea is highly curved. This results in a distorted image and thus any measurements made of structures in an undewarped image, can result in erroneous values. Other distortions are caused by light rays encountering interfaces between media of different indices of refraction. For instance, rays pass from the air (refractive index of 1.000) into the cornea (refractive index of about 1.372), and from the cornea into the aqueous humor (refractive index of about 1.332). Dewarping requires knowledge of the refractive indexes of the cornea and the aqueous humor, as well as the locations of the anterior and posterior corneal surfaces. Dewarping, using only one of the two corneal surfaces, can yield useful information. However, a critical element in the approach to proper dewarping is the ability to segment correctly one (first surface) or more surfaces used in the dewarping procedure.

Upon dewarping, more accurate metrology of the structures found downstream of the corneal surface or surfaces can be performed. For instance, anterior chamber depth and angle can be measured by using the iris and lens segmentation to guide semi- or fully-automatic measurements based on user identification of at least one reference mark in the image: such as the scleral spur but other anatomical items include Schwalbe's line, trabecular meshwork, Schlemm's canal, or a corneal or iris surface or surfaces. The posterior corneal surface and iris segmentations can also be used for semi- or fully-automatic angle measurements (e.g., the iridocorneal angle). Other useful measurements can be geometric metrics of any surface, distance, volume, or interface, applicable to the diagnosis of pathological conditions. These values can be used in planning surgical procedures such as keratectomy, trabeculectomy, and detection of pathologies such as keratoconus.

Reducing the Interference of the Complex Conjugate Images on Real Images

A major artifact in FD-OCT imaging is that of the complex conjugate, which arises from the earlier discussed cross-correlation terms due to the inverse Fourier transform used. The complex conjugate artifact is a mirror image of the true image flipped around the zero-delay—the virtual position where the optical path length in the sample arm equals that of the reference arm. In some cases, the mirror image is distorted due to dispersion mismatch in the two arms of the interferometer, causing it to appear blurred. The complex conjugate artifact can lead to ambiguity in image interpretation as well as erroneous analysis of the OCT data, particularly in the anterior segment. FIG. 1 presents two images of the anterior segment of an eye. FIG. 1(a) is one in which the overlap of real images of iris and corneal structures (real cornea image 102 and real iris image 103) with complex conjugate images of iris and corneal structures (mirror iris image 101 and mirror cornea image 104) hampers adequate analysis of the image. FIG. 1(*b*) is an image that will allow more straightforward identification of features of interest as the various imaged structures of real and complex conjugate are more cleanly separated than those depicted in FIG. 1(*a*).

In many OCT imaging situations, the relative positions of sample and reference arms (the 'delay' position) can be adjusted so that the sample is located entirely in positive or negative space (terms relative to the position of the zero-delay). In this case the complex conjugate part of the image is contained primarily in half of the axial range of the resulting data, and only the real part of the image is contained within the reported axial field-of-view. When imaging the anterior segment of the eye, visualization of multiple structures that extend throughout the entire axial field-of-view of the image is desirable, so limiting the reported field-of-view to half of the acquired data is not an optimal solution.

Several OCT imaging techniques capable of removing or minimizing the complex conjugate artifact have been demonstrated. (In the present application, the terminologies of mirror image and complex-conjugate image are considered to be equivalent.) (See, e.g. Wojtkowski et al. 2002; Yasuno et al. 2006; Wang 2007; Baumann et al. 2007, Zhang et al. 2005, Hofer et al. 2009).

Hardware-based approaches, unfortunately, add cost and complexity to the system, and several approaches have technical limitations. Other techniques rely on specialized algorithms to reduce or remove the complex conjugate artifact (see, e.g., U.S. Pat. No. 8,414,564). The majority of these methods require multiple frame acquisitions and heavy post-processing, which obviates real-time display, visualization, and correction.

Tracking Using Anatomical References in the Anterior Segment

Two critical requirements for successful dewarping of anterior chamber OCT image data are good placement of the corneal surfaces within the available OCT image window to maximize surface coverage, and little or no overlap of the real images with those of the complex conjugate images to permit clean segmentation of the desired surfaces. Both of these require stable control over positioning of the eye of the patient relative to the instrument, and this can be accomplished by tracking.

Due to patient motion, both lateral and longitudinal (i.e., along the scan axis) tracking of eye motion during examination and providing compensation thereto is preferred. Should the patient move longitudinally, as discussed above, then the complex conjugate and real images could overlap, causing segmentation problems, hence deficiencies in the information provided to the dewarping process. Moreover, tracking allows more accurate image registration, accurate placement of anterior segment of structures, and mosaicking of images. Anatomical reference marks for tracking are well-known for the retina, and include at least, the optic nerve head (ONH), the macula, and blood vessels (see, e.g., U.S. Pat. No. 7,884,945). However, these reference marks are not available in OCT anterior segment imaging.

Most OCT systems are optimized for retinal scanning. Anterior segment scans are possible, nevertheless, by the insertion of additional lenses or perhaps by a different optical train in the system. The depth of imaging in the anterior segment poses a severe problem, as the distance between the anterior surfaces of cornea and crystalline lens is 3.5 mm. To reach the posterior surface of the crystalline lens adds an additional 6 mm. Thus simultaneous imaging of a large portion of the anterior segment is currently not possible. Techniques need to be developed to overcome this imaging limitation.

SUMMARY OF THE INVENTION

The systems and methods disclosed herein are aimed to control accurate positioning of the structures found in the anterior segment of an eye of a patient; to improve the ability to dewarp corneal surfaces; and, to provide full-range OCT imaging capability. The positioning control includes appropriate placement of the corneal surfaces within the OCT image as well as maintaining that position during examination (i.e., tracking). One aspect of the accurate positing of the anterior segment is to control the position of the delay which will allow good anterior segment positioning. A method is disclosed which permits fast alignment of the position of the delay and another aspect is presented to track on anatomical structures found within the anterior segment. The embodiments can be used alone or in combination to improve the overall accuracy of measurements made on anterior segment OCT images.

The ultimate goal of anterior segment imaging is to detect and measure specific features in the anterior chamber of the eye, such as corneal surfaces, iris, crystalline lens, and various structural and functional features such as scleral spur, iridocorneal angle, Schlemm's canal, Schwalbe's line, as well as the trabecular meshwork. Controlled anterior segment positioning allows the optimal placement of corneal surfaces to permit more accurate dewarping, a vital prerequisite to obtaining accurate geometric metrics from the imaging data.

Some of the systems or methods described herein can estimate the approximate corneal surface position and find an extremum of an objective function to establish a proper delay line position. For example, a first distance metric between the anterior surface points and a zero-delay position should be maximized or a second distance metric between mirror images and the anterior surface should be minimized but not below a certain threshold. By the use of an objective function, the adjustment of the delay position can be made automatic. The objective function can also have as inputs both of these conflicting distances and it will find the optimum position satisfying both criteria. Alternatively, the OCT adjustments to implement the optimum position can be automatic or reported to a user, perhaps via a GUI, and the adjustment is performed manually.

The separation between real and mirror images can also be accomplished by the use of statistical measures or metrics. The goal being to separate the mirror image from overlapping structures of interest, a statistical metric would identify the location of overlap and report, flag, or automatically adjust the delay to compensate.

In another approach, a watershed line (connectivity of a local maxima), which is derived from distance-transform image processing, is used to separate the overlapped from non-overlapped (real-mirror) images. Distance-transform is well known in morphological image processing.

The combination of precise tracking and optimum placement of corneal surfaces allows accurate automated dewarping to be accomplished. In various embodiments, systems and methods are also presented to achieve more accurate dewarping in the situation where there is limited field-of-view anterior segment imaging, in which there is incomplete detection of one or both of the corneal surfaces. This limitation is overcome by determining more complete information regarding the profiles of these surfaces. More complete information can yield improved accuracy dewarping, which is an important step in realistic geometric measurements of anterior segment structures. The systems and methods presented herein can be fully automated or configured to report the results to a user, who then can implement any suggested adjustments.

BRIEF DESCRIPTION OF THE DRAWINGS

FIG. 1 is of two B-scans, one where mirror images or complex conjugates overlap with real images (FIG. 1(a)) and the other one in which the overlap is such that it does not interfere with the segmentation (FIG. 1(b)). The various structures in the image have been identified for reference.

FIG. 2 is a schematic of a basic FD-OCT optical coherence tomographic instrument.

FIG. 11 is a sequence of manipulated images, for the case of no overlap between the real cornea and mirror image iris; In FIG. 11(a), the real cornea image (1101) is clearly imaged, as are the images of the mirror cornea (1102) and those of the mirror iris (1103)

FIG. 16(a) represents a basic approach. In FIG. 16(b), a preferred method is presented.

FIG. 21 is an OCT B-scan image that could be dewarped by a different embodiment applicable to wide-angle scans.

and posterior (2603) surfaces, which can lead to more accurate dewarping in the area of the angle (2601).

Figure 27:
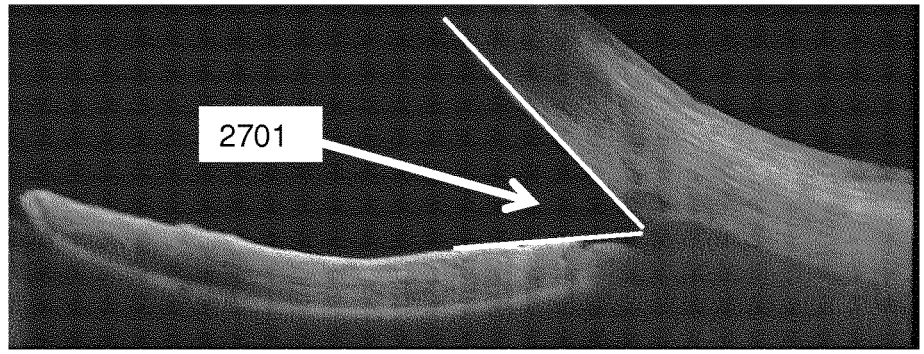

FIG. 27 is a composite image based upon registration and averaging of multiple images taken at the same location followed by image enhancement. The iridocorneal angle (2701) is indicated.

Figure 26:
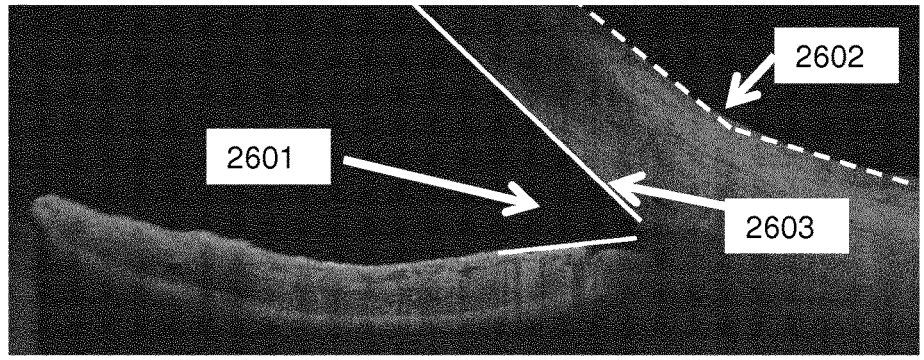
FIG. 26 is an OCT image showing the optimized location of the anterior segment structures within the imaging window. It shows larger segments of both the anterior (2602)
Figure 28:
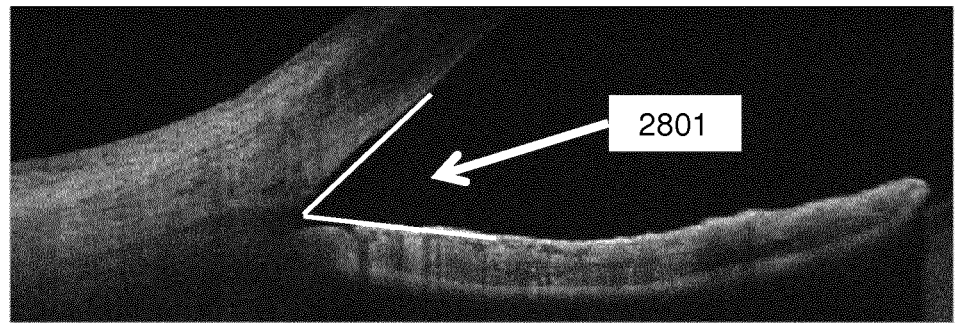

FIG. 28 is an image (intensity or greyscale), like those of FIGS. 26 and 27, and has a field-of-view of 6 mm. This image can be processed using one of the embodiments disclosed in the present application. The iridocorneal angle (2801) is indicated.

Figure 29:
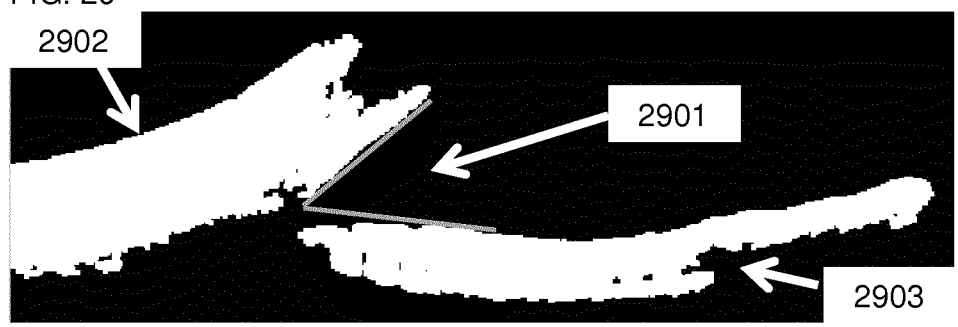

FIG. 29 is a binarized image of FIG. 28: accomplished by a thresholding method followed by simple morphological processing. The final binary image has two components: a stub of the cornea (2902) and a portion of the iris (2903). The iridocorneal angle (2901) is indicated.

Figure 30:
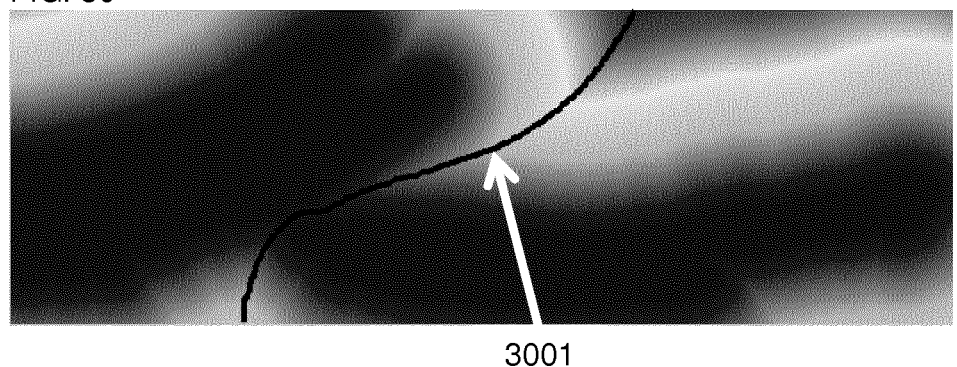

FIG. 30 is a Euclidean distance-transform image of FIG. 29. The watershed line (3001) is indicated.

Figure 31:
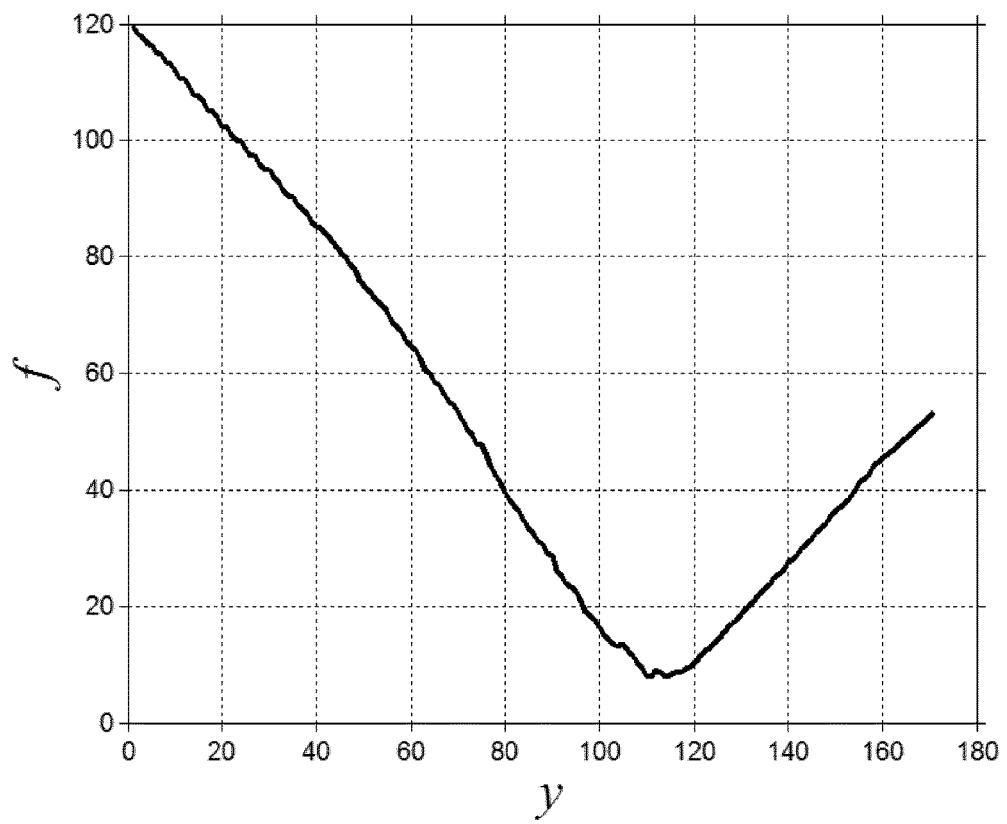

FIG. 31 is a plot of the watershed function $f$ derived from analyzing the image in FIG. 30.

Figure 32:
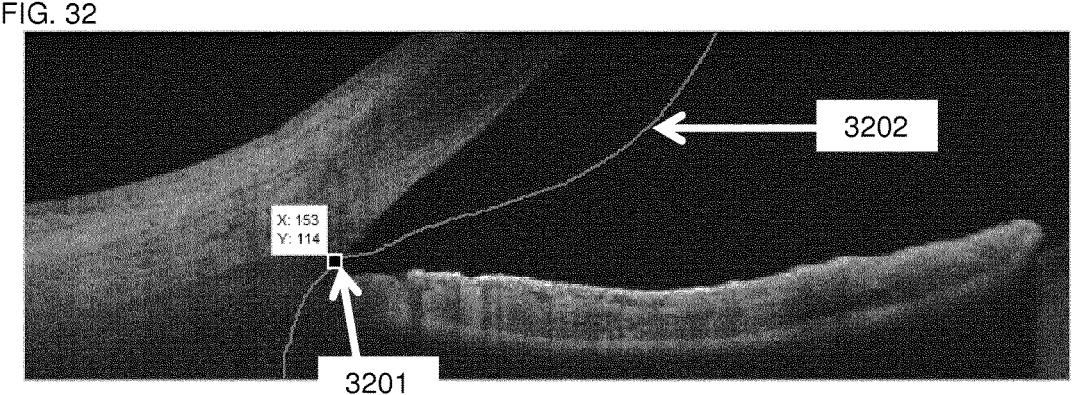

FIG. 32 is FIG. 28 with the watershed function (3202) $f$ of FIG. 31 imposed thereon. The approximate (x,y) position of the scleral spur or apex of the iridocorneal angle (3201) is so marked.

Figure 33A:
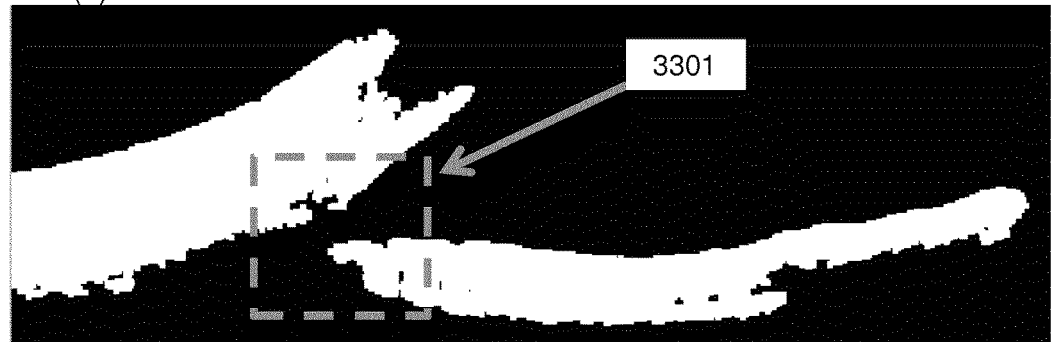
Figure 33B:
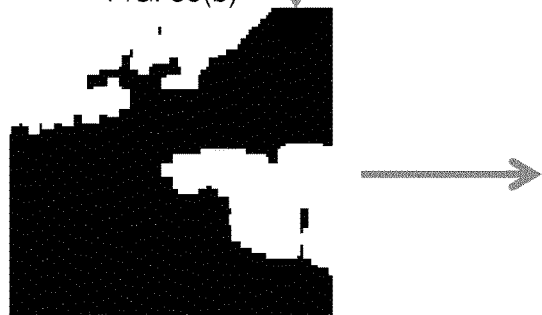

FIG. 33(a) is a repeat of FIG. 29, but with a sub-region or sub-image (3301) marked thereon and separately displayed as FIG. 33(b). A Euclidean distance-transform is applied to FIG. 33(b) to derive FIG. 33(c) and the subsequently derived watershed line (3302).

Figure 33C:
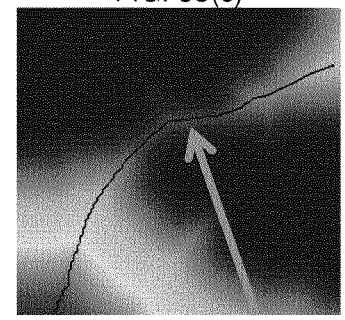
Figure 34:
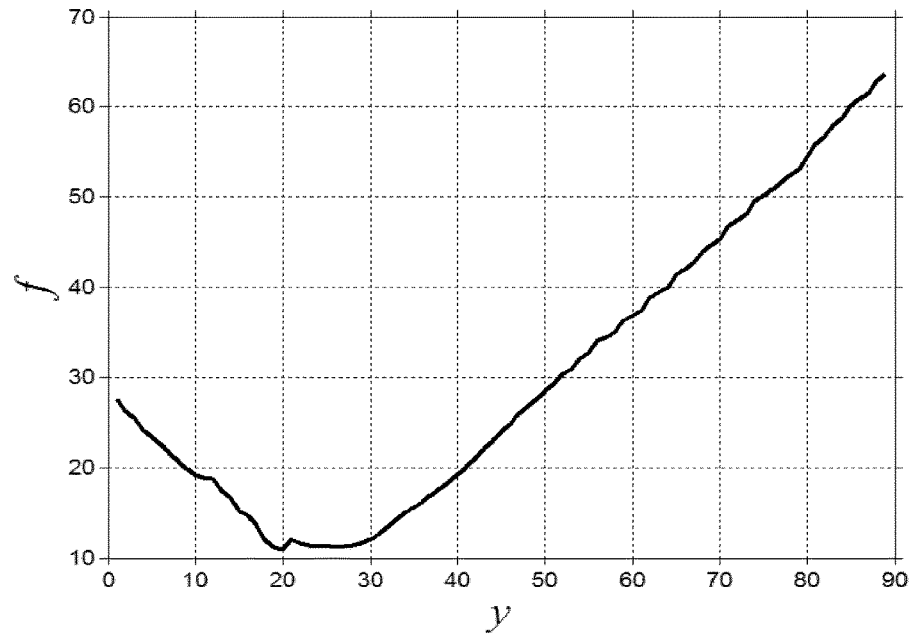

FIG. 34 is a plot of the watershed function derived from FIG. 33(c).

DETAILED DESCRIPTION

A generalized Fourier Domain optical coherence tomography (FD-OCT) system used to collect an OCT dataset suitable for use with the present set of embodiments is illustrated in FIG. 2. An FD-OCT system includes a light source, 201, typical sources including, but not limited to, broadband light sources with short temporal coherence lengths or swept laser sources.

Light from source (201) is routed, typically by optical fiber (205), to illuminate the sample (210), which could be any of the tissues or structures with an eye. The light is scanned, typically with a scanner (207) between the output of the fiber and the sample, so that the beam of light (dashed line 208) is scanned over the area or volume to be imaged. Light scattered from the sample is collected, typically into the same fiber (205) used to route the light for illumination. Reference light derived from the same source (201) travels a separate path, in this case involving fiber (203) and retro-reflector (204). Those skilled in the art recognize that a transmissive reference path or arm can also be used. The delay difference between the reference and sample arms determines what axial locations of the sample is imaged. The delay difference can be controlled by adjusting a delay line in either the reference or sample arms of the system or changing the location of the patient relative to the instrument along the direction of the light path. Delay adjustment as used herein refers to any adjustment that alters the optical path length difference between sample and reference arms. Collected sample light is combined with reference light, typically in a fiber coupler (202), to form light interference in a detector (220) and said detector generating signals in response to the interfering light. The output from the detector is supplied to one or more processors (221). The results can be stored or further processed in one or more processors and/or displayed on display (222).

The processing and storing functions may be localized within the OCT instrument or functions may be performed on an external processing unit to which the collected data is transferred. This unit could be dedicated to data processing or perform other tasks which are quite general and not dedicated to the OCT device. The display can also provide a user interface for the instrument operator to control the collection and analysis of the data. The interface could contain knobs, buttons, sliders, touch screen elements or other data input devices as would be well known to someone skilled in the art. One or more of the processors can be of the parallel processing type such as GPUs, FPGAs, or multi-core processors. As FIG. 2 is a generalized OCT instrument, typical instruments are normally configured to image the retina. To image the anterior segment, the optical configuration of the system can be modified by the insertion of additional lenses and an adjustment to the delay between the sample and reference arms.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample. The scattering profile as a function of depth is called an axial scan (A-scan). A set of A-scans measured at neighboring locations in the sample produces a cross-sectional image (tomogram or B-scan) of the sample. A collection of B-scans makes up a data cube or volume. It should be noted, however, that the application of these methods need not be limited to data acquired via FD-OCT; they could also be applied to data acquired via other OCT variants including TD-OCT and could be applied to parallel OCT techniques such as line field, partial field and full field as well as traditional point scanning systems.

The sample and reference arms in the interferometer could consist of bulk-optics, fiber-optics or hybrid bulk-optic systems and could have different architectures such as Michelson, Mach-Zehnder, or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are typically used at the detection port for SD-OCT systems. The embodiments described herein could be applied to any type of OCT system that uses an inverse Fourier transform.

Optimum Placement of Structures within OCT Anterior Segment Images

An automated alignment and acquisition of OCT anterior segment imaging would allow fast alignment of the OCT system in the presence of unwanted artifacts due to overlap of complex-conjugate images with real images.

Figure 3A:
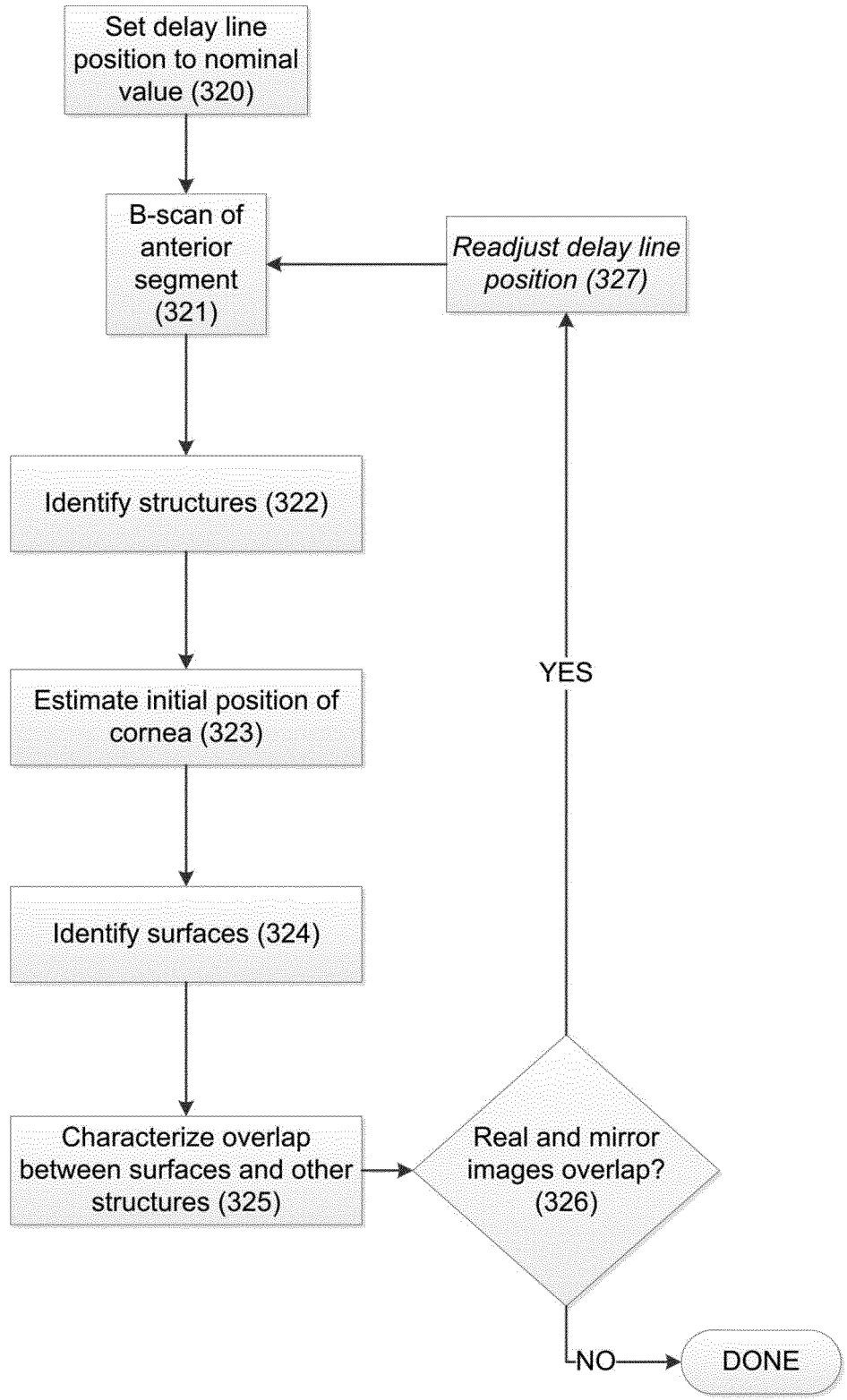
FIG. 3(a) is a flow chart outlining the basic method to discern an overlap between structures of interest and unwanted structures.

A generalized embodiment to achieve optimum placement of structures within OCT anterior segment images imaging technique is summarized in FIG. 3(a). In this approach, the delay is set to some nominal value (320) and OCT image data, in this case a B-scan, is obtained (321). The B-scan is then processed to identify any structures (322) therein and to locate an initial corneal position (323) and then to identify within the identified structures surfaces of the cornea (324). The next step is to characterize the overlap between various structures and surfaces (325) and to decide if there is an overlap (326). If an overlap still exists, the delay position is readjusted (327) and the procedure repeated until no overlap exists.

Figure 3B:
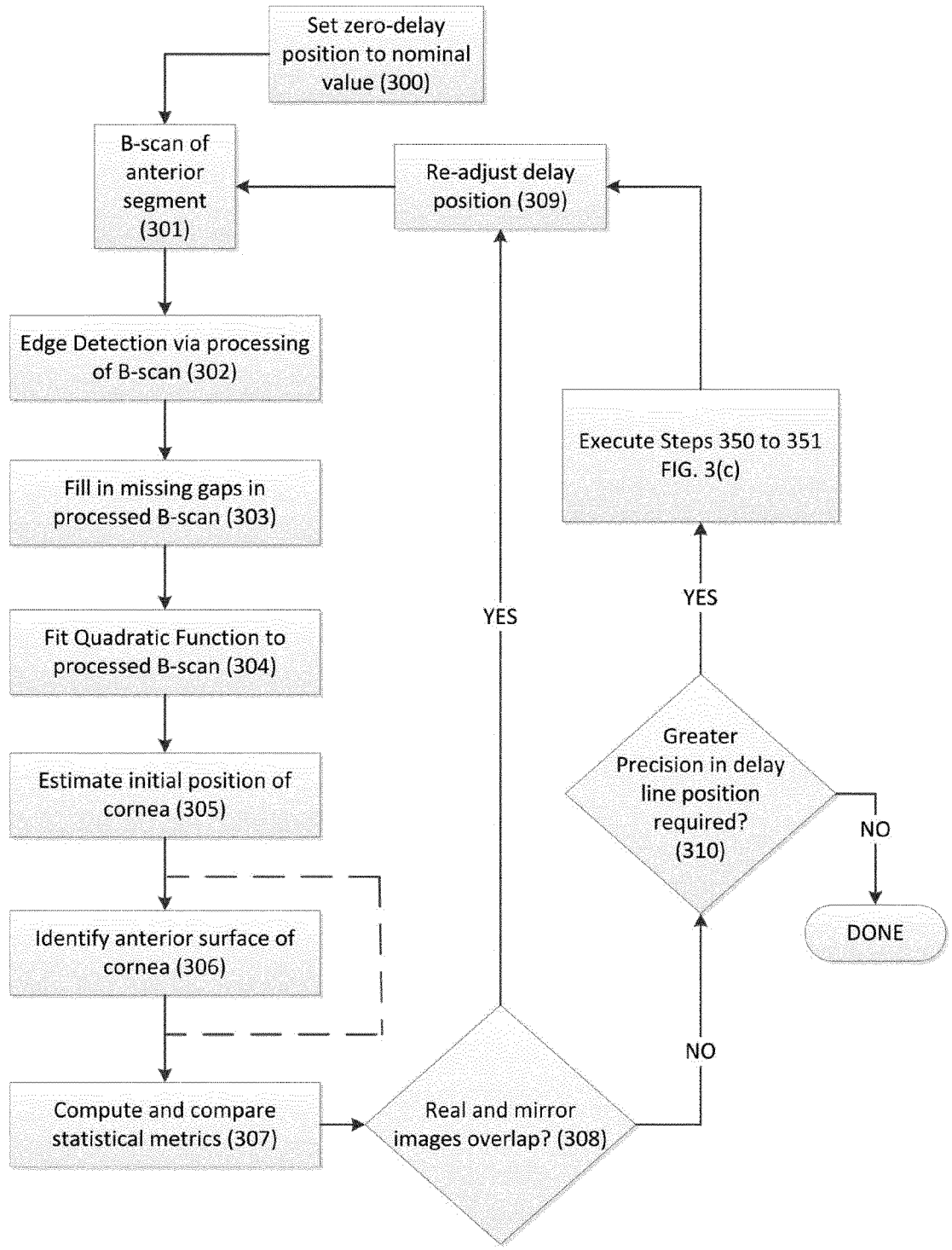
FIG. 3(b) is a flow chart outlining a preferred method of the present application.
Figure 3C:
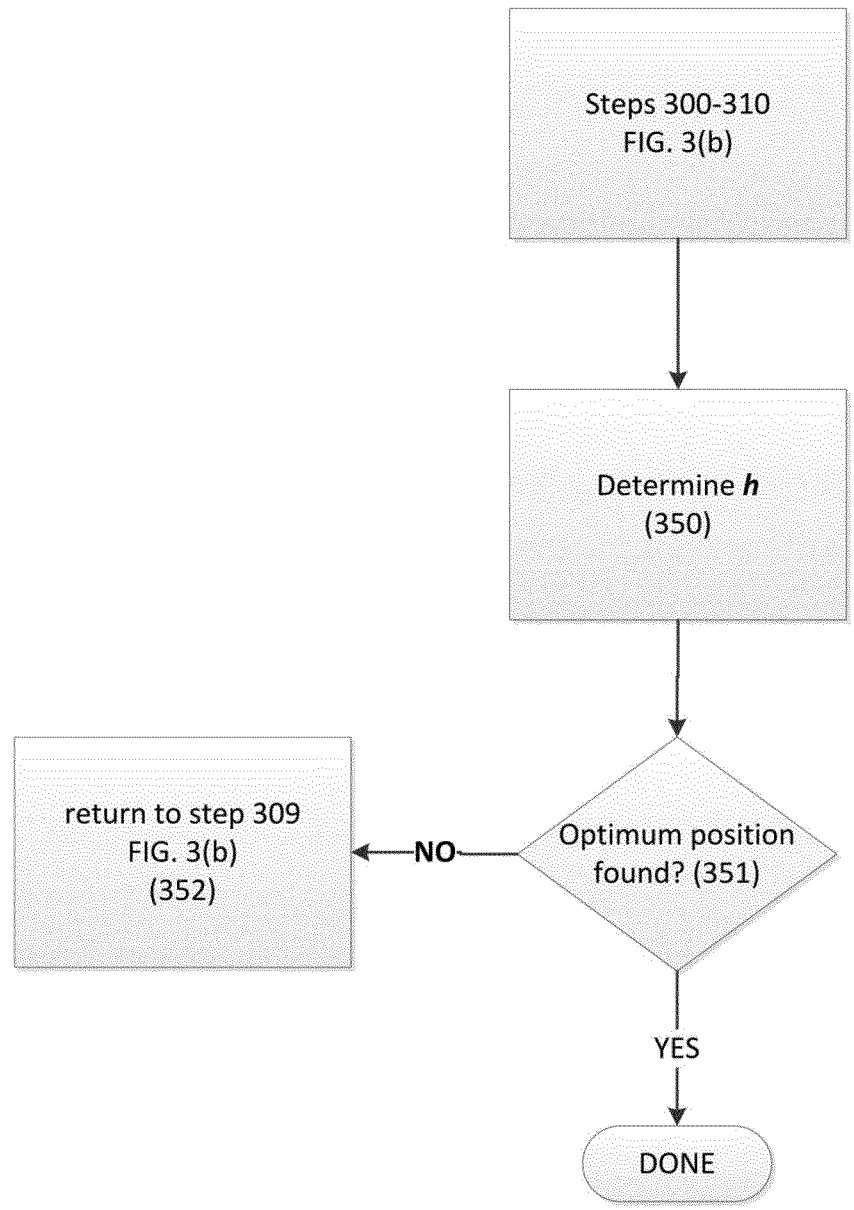
FIG. 3(c) is a procedure to obtain a more precise position for the delay and is an optional addendum to the method depicted in FIG. 3(b).

A preferred embodiment is presented in FIG. 3(*b*). The first step is to set the expected delay position to some desired or nominal value (300) and obtain a B-scan of the anterior segment (301). If desired, this image can be re-sampled to a smaller size to reduce computational time. An example of an anterior segment B-scan intensity image is given in FIG. 4. In this figure, the real image of the cornea is clearly depicted (401). However, near the central part of the cornea (401) and above it, are complex-conjugate images of surfaces of the iris (403). One surface of this mirror image, overlaps the anterior corneal surface. Such an overlap will cause automatic segmentation to fail.

Figure 4:
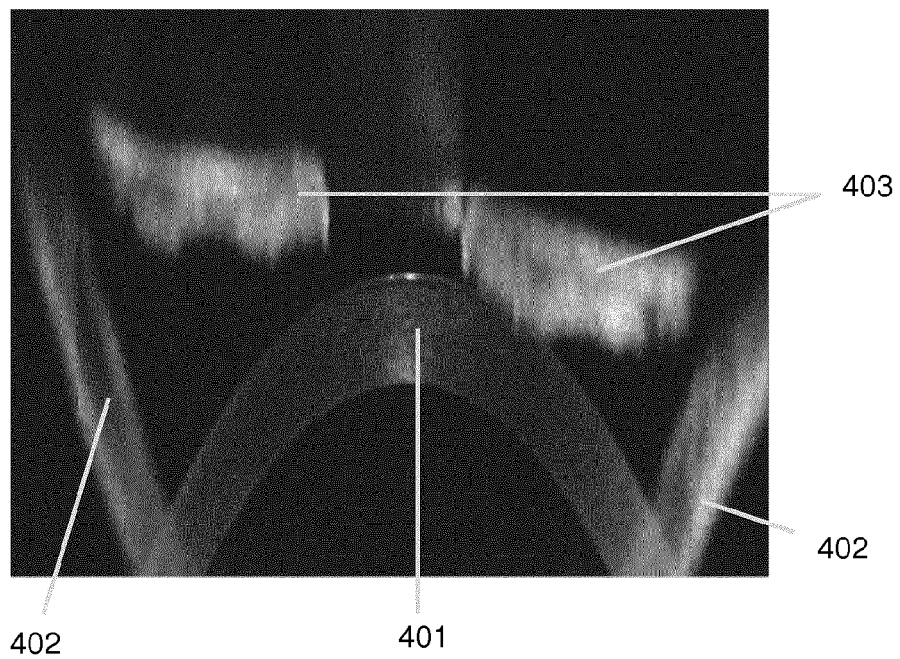
FIG. 4 is a B-scan of the anterior segment of the eye. The structures in this image are the real cornea (401), the mirror cornea (402), and the mirror iris (403).
Figure 5:
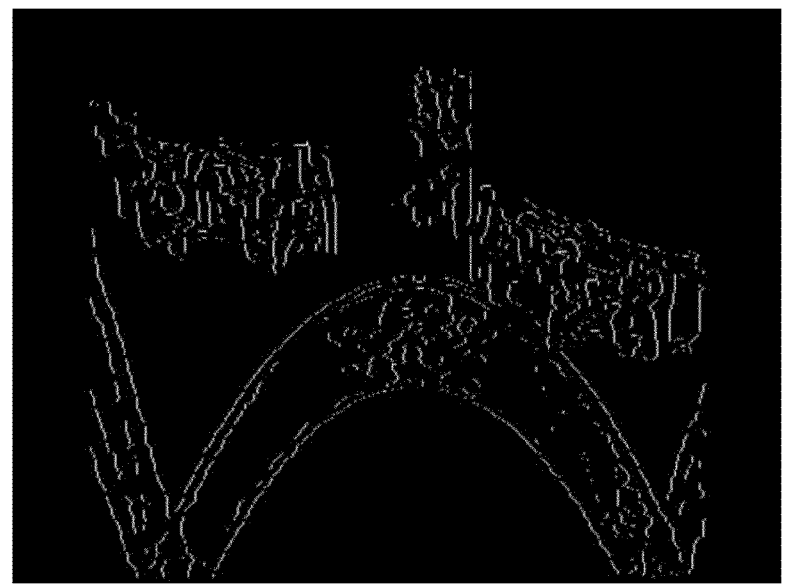
FIG. 5 is a processed version of FIG. 4. The former has undergone edge-detection to produce an edge image.

To enable the identification of structures within the image data, edge detection (302) is then performed on the B-scan image or its reduced-size version. This procedure ultimately results in an edge image where a pixel having a "1" value represents an edge (see, e.g., Canny 1986). A gradient image is converted into an edge image by applying a threshold. Any pixel value greater or equal to a pre-defined value is given the value of one. Any pixel value not satisfying this requirement is given the value of zero. The skilled person in the art will readily recognize that determining threshold values is a standard art (see, e.g., Parker 1997). FIG. 5 presents the edge image of FIG. 4.

While the Canny edge detection is the preferred algorithm, other approaches, with subsequent pixel thresholding/binarization, would be tractable as well. The Canny algorithm converts the initial intensity image into a gradient image by the use of some derivative function such as that of a derivative Gaussian. Canny edge detection produces an edge image that contains most likely all the desired anterior surface edges, as well as undesired edges from other surfaces. Besides the use of this functional characterization, optional functional forms that could be convolved with the intensity data in the axial dimension to create a gradient image are Prewitt or Sobel operators, Laplacian, Kirsch compass, Marr-Hildreth, difference of Gaussians, Laplacian of Gaussians, higher-order Gaussian derivatives, Roberts cross, Scharr operator, Ricker wavelet, Frei-Chen or any discrete differentiation operator well known to the ordinary skilled person in the art.

Additional approaches can use multi-scale techniques such as Log-Gabor wavelets and phase congruency (Kovesi 2003) to generate gradient images and extract image features to aid in the identification of structures within the image. Phase congruency is highly localized and invariant to image contrast which leads to reliable image feature detection under varying contrast and scale. The method of phase congruency applies to features with small derivative or smooth step where other methods have failed.

Within the edge image, there are gaps between neighboring segments (which consist of several adjacent points). These gaps can be connected (303) by searching at the end of such a segment, within a specified radius, to locate any points, or other segment endpoints that lie within said radius. A problem exists in that the origins of these edges are not readily identifiable and thus cannot be used without further processing. The edge information is used to estimate the initial positions of the anterior surface (for example in the application of step 305 in FIG. 3(*b*)). Connected edges with a length smaller than a predetermined threshold can be removed to reduce the execution time in the next step.

Once the gaps have been filled, quadratic functions (or any other even function that fits well a 2D-slice through the corneal structure, which is naturally very close in shape to a conic curve) are then robustly fitted to identified connected edges (304). The number of quadratic functions that are fitted depends on the number of connected edges found in the image or sub-image or region-of-interest (ROI). This number may be significantly more than the anatomical edges found in the sample because many of the "edges" identified by Canny edge detection (or other edge detection algorithms) may be due to noise or due to the mirror images.

Figure 6:
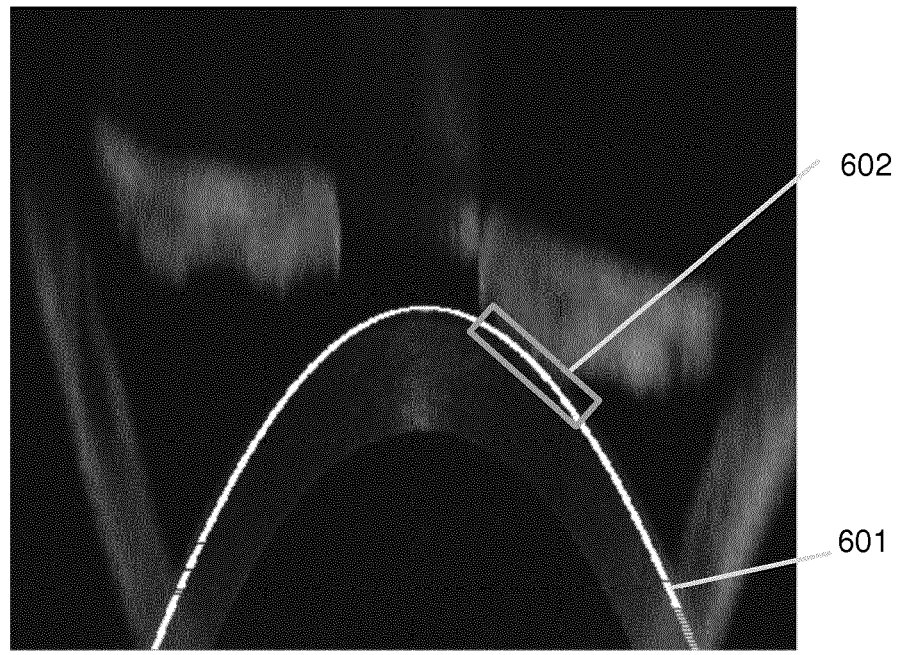
FIG. 6 shows a parabolic fit (601) using RANSAC algorithm to the anterior corneal surface of FIG. 5, but placed onto the intensity image of FIG. 4. The area of overlap between the real corneal anterior surface and the mirror iris image is enclosed by the rectangle (602).

The fitting function with the simplest form, that of a quadratic function, is a parabola ($y=ax^2+bx+c$). This quadratic function's parameters can be determined using Random Sample Consensus (RANSAC) fitting (see Fischler & Bolles 1981). From the quadratic functions fitted to the connected edges (see 601 of FIG. 6), a surface is initially identified as corresponding to a corneal surface (305) and this initial surface is used for the initial estimates to identify and to locate the actual anterior surface position (306). (If the identified corneal surface is that of the anterior or posterior corneal surface, the other surface is locatable by assuming a thickness model.) This quadratic function is selected based on a number of known characteristics: first, the quadratic function is assumed to have a concave shape, with that curvature falling within the known range of corneal anterior curvatures; second, its vertex is assumed to be located in the central part of the image in the lateral or transverse dimension. (This would be canonically known as the x-dimension, with the z-dimension corresponding to the axial or A-scan direction.)

In FIG. 3(*b*), the dotted line that obviates the step 306 is an option should a faster algorithm be desired, such as for real-time determinations.

Figure 7:
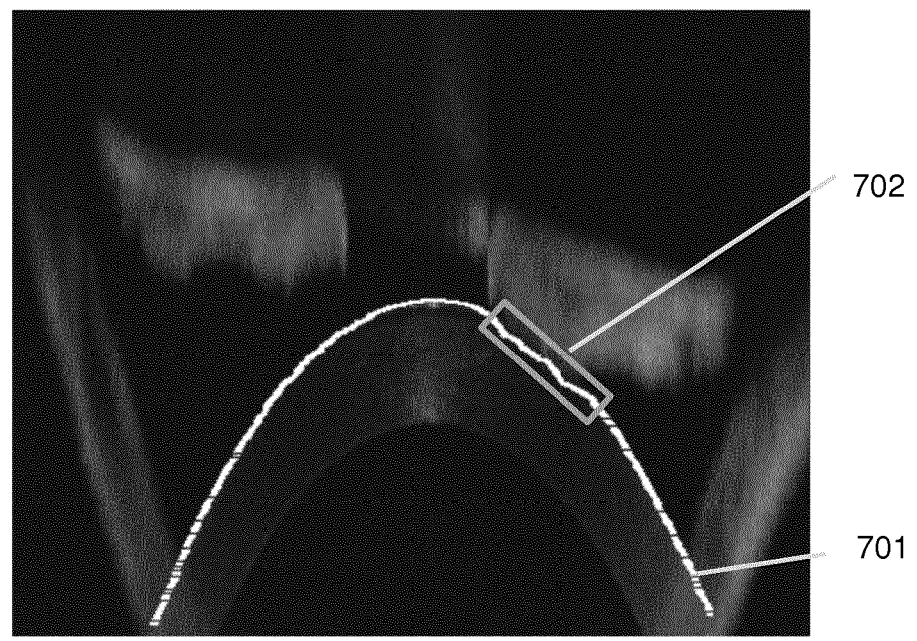
FIG. 7 shows a segmentation (701) (also using RANSAC) to the corneal image of FIG. 4. The segmentation has a problem in the area of the overlap with the iris mirror image. The area of overlap between the real corneal anterior surface and the mirror iris image is demarcated by the rectangle (702) as it is in FIG. 6.

The coordinates of the connected edges (in the edge image) associated with the quadratic function represent the anterior (or posterior) surface (inliers detected by RANSAC). Any discontinuities in the anterior surface can be removed by using a fast edge-linking algorithm (for example, in the application of step 303 in FIG. 3(*b*)) to generate connected surface points (701) as shown in FIG. 7. (For information regarding edge-linking algorithms, see, e.g., Umbaugh 2010.) FIG. 7 shows a segmentation (701) (also using RANSAC) to the corneal image of FIG. 4. The segmentation has a problem in the area of the overlap with the iris mirror image. The area of overlap between the real corneal anterior surface and the mirror iris image is demarcated by the rectangle (702) as it is in FIG. 6.

Statistical metrics of a small region above the anterior surface can be derived and compared to background statistical metrics of a similar nature (307) and this comparison (308) indicates whether the central cornea intersects with the mirror of the iris or lens surface. Statistical metrics could include statistical dispersion and/or moments such as mode, mean, median, skewness, kurtosis, of distributions of pixel values in desired sub-images. Other statistical analyses to identify a region or sub-image with an excess of intensities above the background would be readily apparent to the skilled person in the art.

A decision (308) is then possible as to whether the initial estimated value of the position of the delay is sufficiently accurate for the purposes at hand or is a more refined value required. If overlap persists, then the delay-line position is readjusted (309), and the method repeated.

For greater precision in determining the optimum position of the delay there exists an extension to the method of FIG. 3(*b*) which is given by steps 350 to 351 in FIG. 3(*c*). The initial or actual anterior corneal surface points (defined as Set A) and zero-delay positions in the image (defined as Set B) can also be used to find an optimal alignment position by the global maximization of the Hausdorff distance (h) between these two sets of points. After setting the delay position to some initial value, which could be based upon the rough position determined in the steps 300-309 of FIG. 3(*b*), then the Hausdorff distance (h) is determined as a function of Δ (350). The optimum delay line position is the position that maximizes the Hausdorff distance between set A and set B. The delay arm position is easily determined by standard techniques (e.g., by a change in slope of the curve or steepest decent optimization). The dependent variable 'h' is an objective function (or cost function) known in mathematical optimization and Δ is the position of the delay. If the optimum position has been determined (351), then the procedure is terminated. The alternative (352), in the case of no optimum position, is to return to the coarser method of FIG. 3(*b*).

The Hausdorff distance (h) measures how far two subsets of a metric space are from one another. Two sets are close in the Hausdorff distance if every point of either set is closer to some point of the other set. Note that zero-delay points are considered as those points within the lateral endpoints of the anterior surface. The objective function based on the Hausdorff distance defined as follows $$\max[h(A,B)], \text{ where } h(A,B)>0, \text{ and,}$$

$$h(A,B)=\max\{\min[\text{abs}(a-b)]\}, \text{ where } a \in A, b \in B, \qquad \text{(Eq. 1)}$$

and set A represents the set of point of the anterior surface; and the set B represents the points of the zero-delay positions in the image.

While this embodiment has used the Hausdorff distance, any objective function appropriate to defining non-overlapping real and complex-conjugate images could be used. Such functions are standard in optimization techniques. The determination of the extrema (minimum or maximum) of such functions leads to the optimum solution. An objective function may have a variety of components (vs just one) in which it can find the optimum position while compromising potential conflicts between the components. One such function (or metric) might be a weighted sum or a product of the cumulative values within certain pre-determined areas. In this case, the dependent variable used in steps 350 and 351 of FIG. 3(*c*), h, would be the objective function.

In an alternative aspect of the present application, if the shortest distance ($=d_{sh}$) between the vertex position of the anterior surface and the zero-delay is smaller than a threshold, then there will be unwanted image overlap. The delay position will then need to be adjusted accordingly and the process repeated until the threshold distance has been met (meaning a clean separation between mirror and real images). Techniques for determining a threshold value are well-known to the skilled person in the art (see, e.g., Parker 1997). Alternatively, the threshold may be known in advance for a particular instrument during calibration.

Another method of characterizing overlap of real and complex conjugate images lies in deriving a watershed line or function. A grey-level image (an OCT B-scan, for example) may be seen as a topographic relief, where the grey level of a pixel is interpreted as its altitude in the relief. A drop of water falling on a topographic relief flows along a path to finally reach a local minimum. Intuitively, the watershed of a relief corresponds to the limits of the adjacent catchment basins of the drops of water. In image processing, different types of watershed lines may be computed. Watersheds may also be defined in the continuous domain, which is in the context used in the present application. There are many different algorithms to compute watersheds. Watershed algorithms are often used in image processing primarily for segmentation purposes. A watershed line is obtained by performing a distance transform on a binarized image. A common distance transform is Euclidean, although other transforms are also applicable to this problem, as would readily be recognized by the ordinary skilled person in that art.

In the current application, a watershed line will possess continuous connectivity if there is no intersection or overlap of a mirror image with that of a real image. These two images, real and mirror, are the catchment basins referred to above. If there is overlap between the real and mirror images, then the watershed line will not be continuous, and will not exist in the regions of overlap. (Additional information on watershed function or line, may be found in Meyer 1994; or any standard text on morphological image processing, such as Russ 2011.) The watershed is derived from a distance-transform image and the length of the watershed (or the connectivity of local maxima) in the region above the anterior corneal surface can identify an overlap.

Figure 8:
FIG. 8 is the thresholded/binarized image of FIG. 4.
Figure 9:
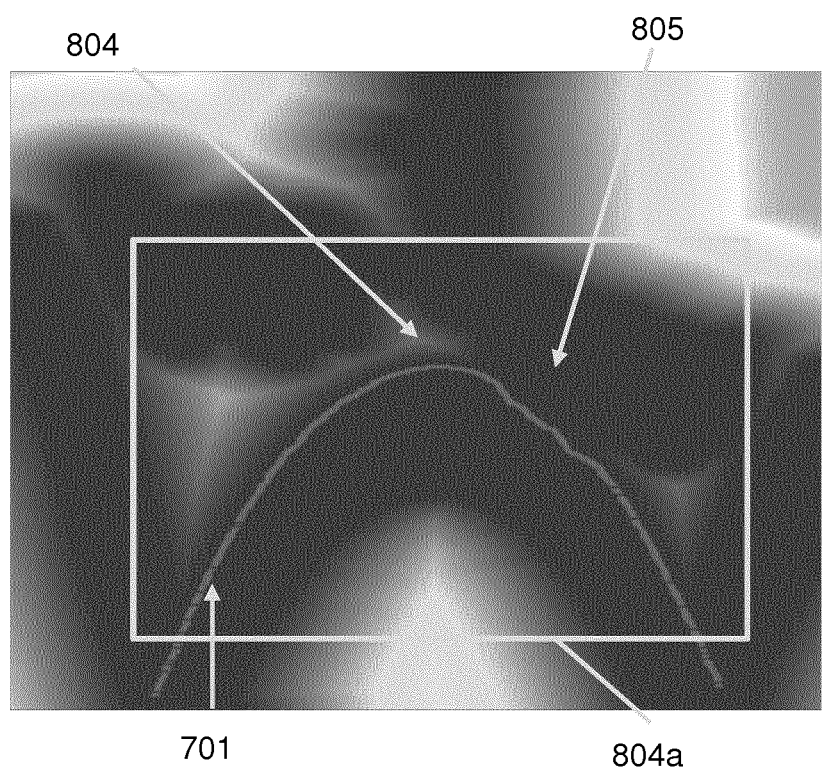
FIG. 9 is a distance-transform image of FIG. 8. Identified are the local maxima (804) above the segmentation fit (701) (showing the location of the corneal anterior surface as a reference). Also shown is the selected region-of-interest (ROI) (804a). Other regions or shapes could also be chosen.
Figure 10A:
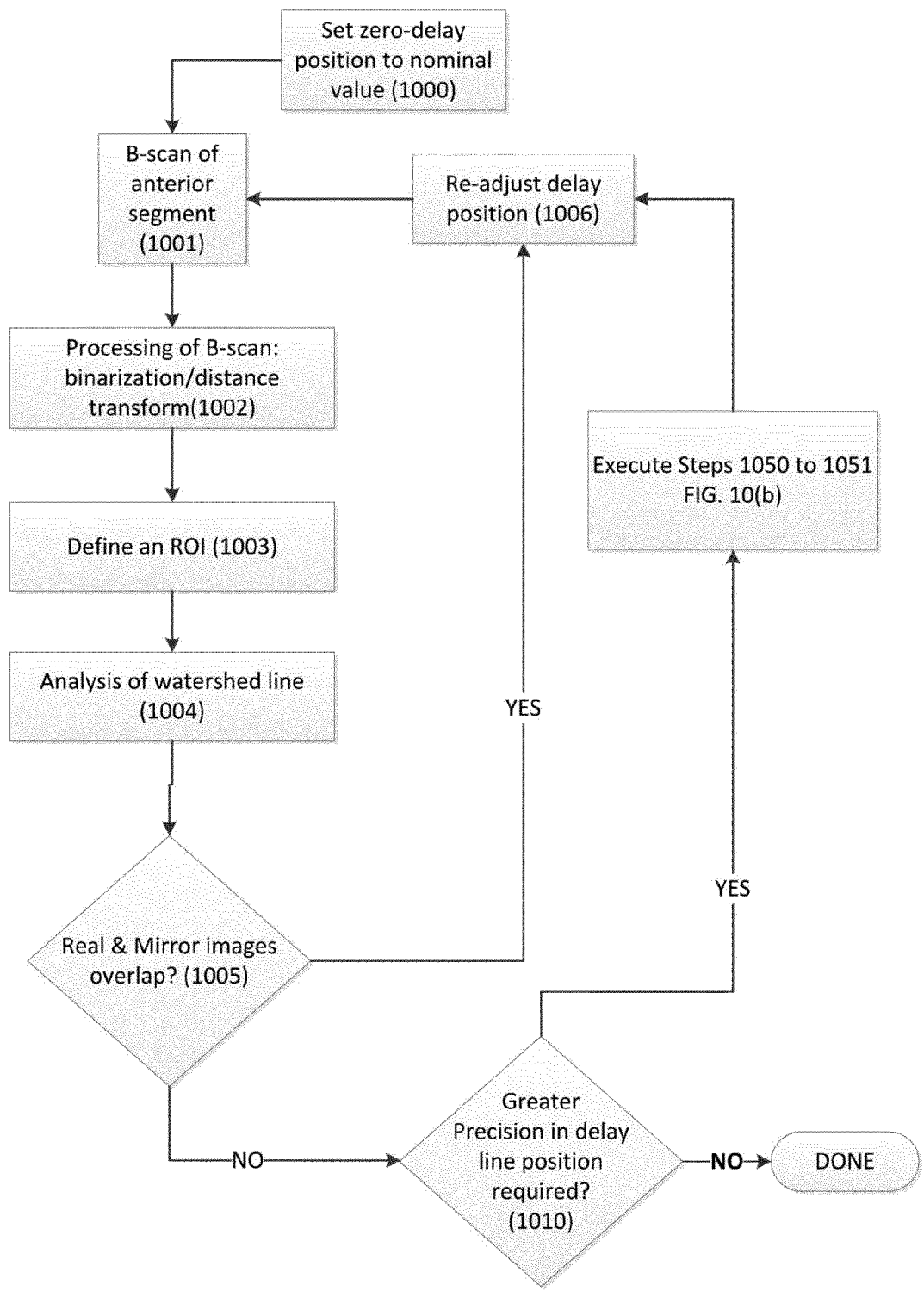
FIG. 10 presents a method of accomplishing automatic determination of the delay position using a watershed line (connectivity of local maxima). The basic embodiment is given in FIG. 10(a). An extension to the method of FIG. 10(a) for greater precision in the determination of the optimal value of Δ is given in flow chart of FIG. 10(b).
Figure 10B:
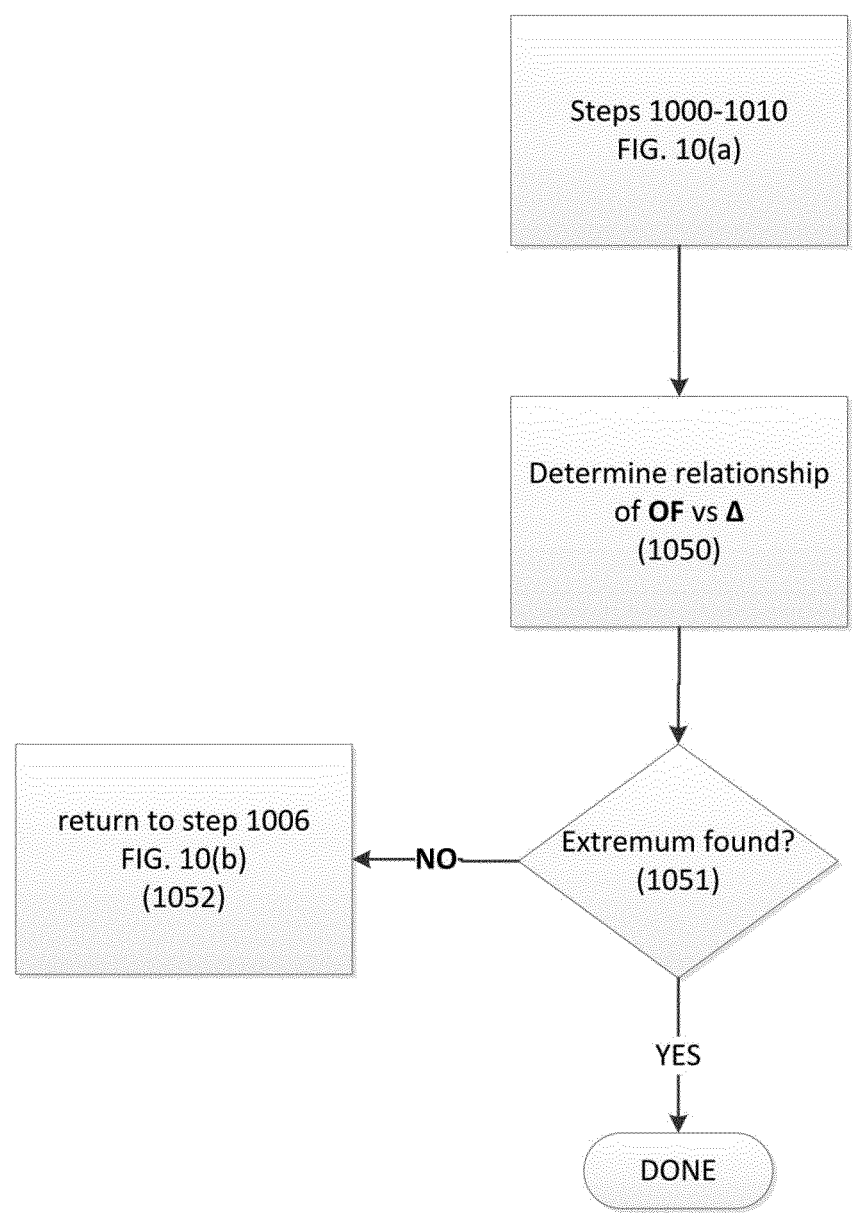
Figure 11A:
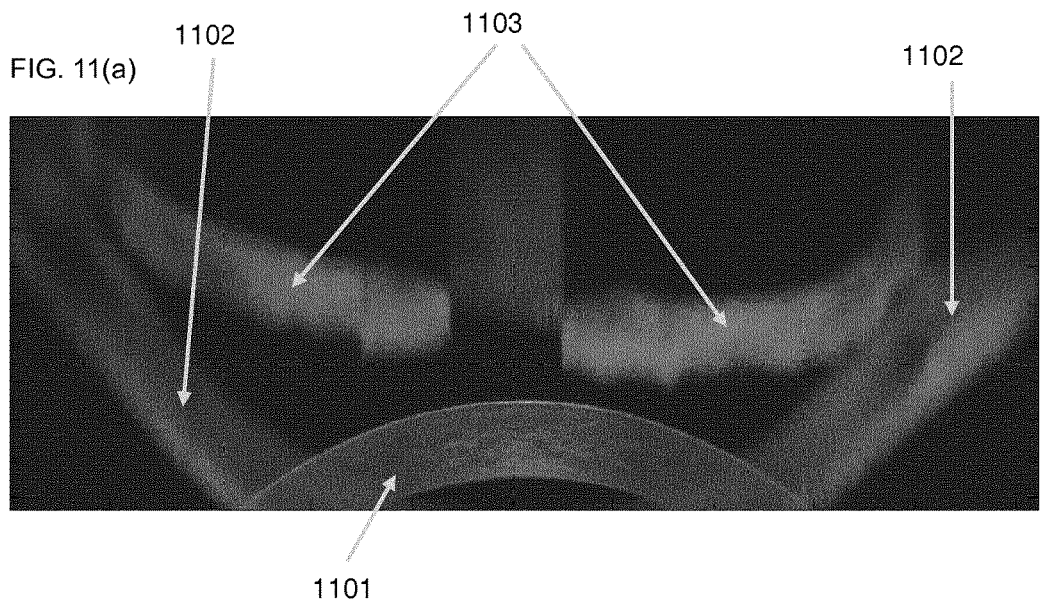
FIG. 11(a) is the original intensity image.
Figure 11B:
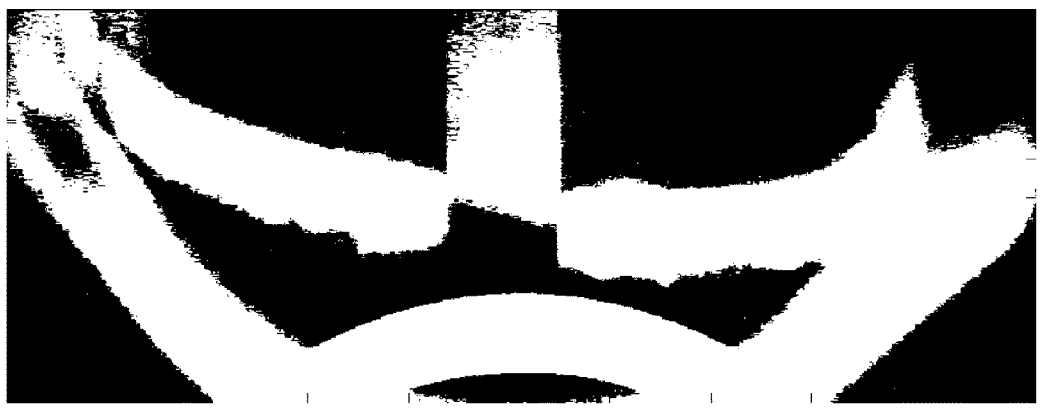
FIG. 11(b) is the binarized/thresholded image of FIG. 11(a)
Figure 11C:
FIG. 11(c) is the inverted image of FIG. 11(b)
Figure 11D:
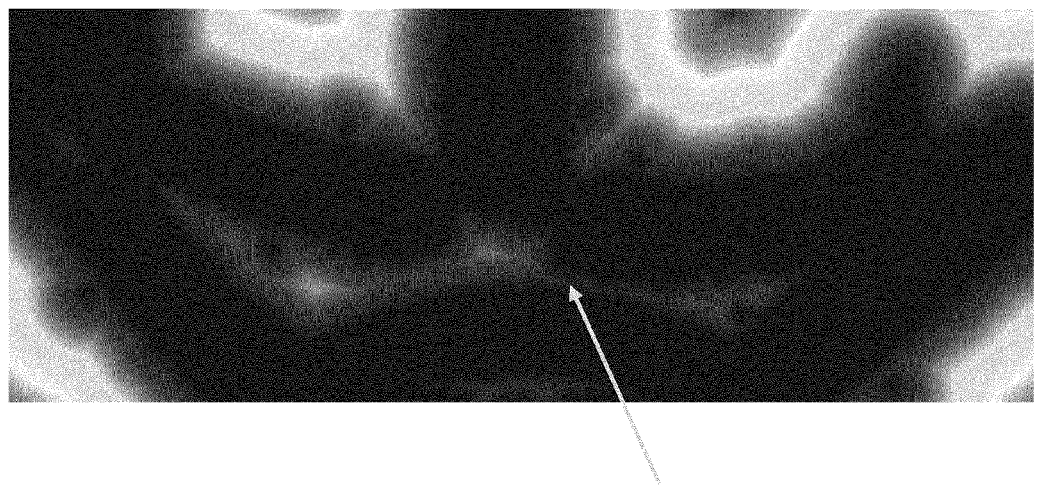
FIG. 11(d) is the distance-transformed image of FIG. 11(b). The watershed line is shown (1104).

FIG. 10(*a*) is a basic flow chart of this embodiment. An initial position for the delay is set (1000) and a B-scan of the anterior segment is obtained (1001), which should include at least the central portion of the anterior corneal surface. FIG. 4 is an example of the type of image obtained. This B-scan is then processed (1002) by binarization/thresholding yielding FIG. 8 and then by a Euclidean distance-transform resulting in FIG. 9. The computations to convert FIG. 4 in to FIG. 8 are very well known in the art of morphological imaging processing.

Also displayed on this FIG. 9 is the segmentation curve (701) presented as part of an embodiment previously presented that uses statistical metrics to guide the separation of mirror and real images about the position of the zero-delay. It is presented only for reference or guidance: the curve 701 overlaid on this image is not part of the current embodiment. Above this segmentation curve is another curve of local maxima (identified as 804) obtained from the distance-transform. This curve is the watershed function (or line or curve).

A region of interest (ROI) is then extracted (1003) from the distance-transform image, where the ROI can be defined as the upper half of the original image, shown as the box (804*a*) in FIG. 9. This ROI contains the upper portion of the anterior and posterior corneal surfaces. An ROI (804*a*) can be defined as a central 6 mm zone in the lateral direction in FIG. 9 as an example. But other sizes and shapes for the selected ROI can be used for a particular purpose. The connected components of local maxima (the watershed line) within the ROI of the distance-transform image have the possibility of representing one or multiple paths above the central anterior surface. These paths, derived from the local maxima, can be used as indicators (1004) as to whether the central cornea intersects with the mirror of the iris or lens surface. For instance, if multiple disconnected paths (watershed lines) were found, then an intersection or overlap is present.

In contrast, a single long path indicates that no intersection occurred between the laterally central or upper corneal surfaces and the mirror of the iris or lens surface. Iterating on this procedure (1005) can then determine an optimal value for the delay position (Δ) by re-adjusting Δ (1006) and repeating the steps. FIG. 9 has imposed upon it a segmentation (701) in order to show the situation when there is overlap. (The segmentation displayed in this case is shown only for reference; it is not part of this particular embodiment.) Should greater precision be required, there exists an extension given in FIG. 10(*b*) (1050-1051) to the method of FIG. 10(*a*); the distance-transform image of FIG. 9 can also be used to find an optimal alignment position by the minimization of the sum of connected local maxima as an objective function (OF). This extension (1050) would generate the relationship of OF vs $\Delta$ (position of the delay), find the desired extremum (1051), and the set the delay position accordingly so that the OF is at the extremum found. An extremum can be located by standard techniques, such as locating the point of zero-slope of the relationship, or by steepest-decent techniques. Should this procedure fail to obtain an extremum, the procedure is then to return (1052) to the procedure of FIG. 10(*a*), to obtain a first-order estimate for the extremum.

A connectivity metric can be defined which could be any of the following or any weighted combination thereof: sum, mean, or a distribution of the values in the distance transform image along the watershed line. The shape of this distribution, quantifiable by standard analyses of distributions (kurtosis, skewness, mean, median, mode, various moments as well) would identify the 'connectivity' of the watershed line. Also a plot of the position of the local maxima as a function of the lateral coordinate (within a range of lateral coordinates) would identify gaps in the distribution in the case of a lack of connectivity and would be a continuous distribution within the given range of lateral coordinates. The range would be derived in advance during a calibration phase of the instrument.

Thus in the aforementioned, two image quality metrics have been defined: statistical metrics and connectivity metrics. These can be used to determine optimal positioning of the delay. The calculated adjustment in the delay position can be performed automatically or reported to the operator who then can implement the change manually.

Optimal corneal positioning can be accomplished when there is no overlap between the mirror images of the iris (or crystalline lens). FIG. 11 shows a sequence of images just for this case. The primary goal of the approach is to maximize the amount of corneal surface visible in the imaging window. In FIG. 11(*a*), the intensity image shows that there is no overlap between the mirror and real images. In FIG. 11(*a*), the real cornea image (1101) is clearly imaged, as are the images of the mirror cornea (1102) and those of the mirror iris (1103).

Another improvement in the amount of corneal surface imaged can be accomplished by decreasing the distance between the anterior corneal surface and the nearest surface of the mirror iris image, to a value that is not below a certain minimum or threshold (the second distance metric). This distance determination can be based upon the afore-disclosed embodiments. For example, converting FIG. 11(*a*) into a binary image yields FIG. 11(*b*). (An optional approach is to also invert the contrast transfer function of this image, into a negative image, as in FIG. 11(*c*)). Using either FIG. 11(*b*) or 11(*c*), a distance-transform can be performed (the image in FIG. 11(*d*)) and the watershed function (1104) derived therefrom. This contour would be readily recognized by the ordinary skilled person in the art of morphological image processing as the watershed line. If there is connectivity of this function over a range of lateral coordinates, then there is clean separation between mirror and real images. An iterative approach can then be performed moving the delay position until these two images are no closer than a certain threshold, so as to prevent overlap. Although FIG. 11(*d*) is derived from FIG. 11(*b*), an alternative is to use FIG. 11(*c*) and perform a skeletonization, a technique known by the ordinary skilled person in the art of morphological image processing. This technique possesses the advantage of preserving the connectivity of structures found in the images.

Dewarping

OCT has become an important tool for assessment of pathologies or irregularities of structures found within the anterior segment or chamber. However, measuring an angle or any geometric structure in anterior segment OCT images before corrections for beam geometry or refraction leads to inaccurate values. To correct for refraction error, one needs to detect the anterior and/or posterior corneal surfaces in the image. Often these surfaces are partially captured in a scan's field-of-view as shown in the FIGS. 12 and 13 due to the limited imaging window or depth range of current OCT systems.

Figure 12:
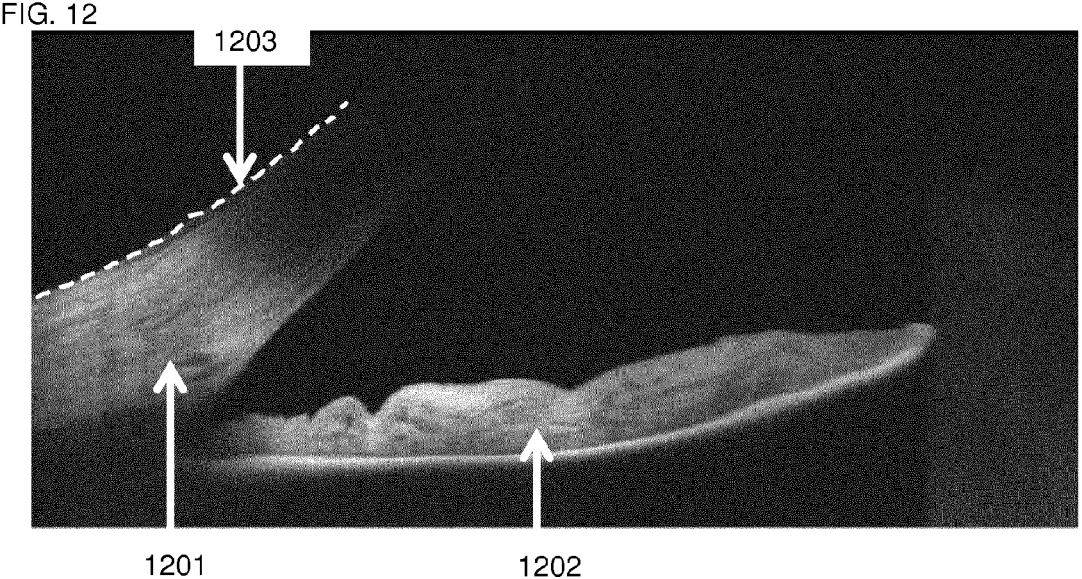
FIG. 12 is an image of a portion of a meridional B-scan of the cornea and approximately includes the interface between the cornea (1201) and the iris (1202). Shown in this figure is the anterior surface segmentation (1203) (dashed-curve) based upon the partially captured anterior surface points.

FIG. 12 shows a portion of the cornea (1201), and a portion of the iris (1202), which is to the left of the crystalline lens (not seen in this view). The segmentation of the anterior corneal surface (1203) is indicated in this figure.

Figure 13:
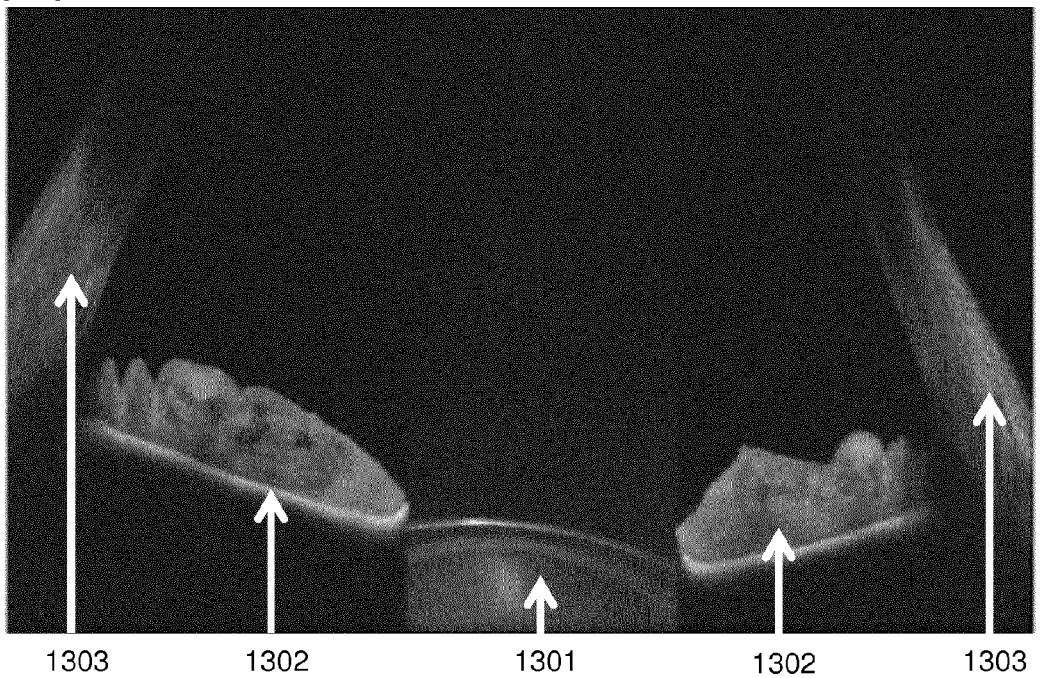
FIG. 13 is an OCT B-scan image of part of the anterior chamber of the cornea and shows part of the cornea (1303), the iris (1302), and a portion of the crystalline lens (1301).

In FIG. 13, a wide field image, the cornea (1303) is indicated, as is the crystalline lens (1301), and the iris (1302) as well.

If it is desired to measure accurately the iridocorneal angle, then, at a minimum, the measurement points need to be correctly dewarped. The segmentation of anterior and/or posterior surfaces of the cornea are used as refractive surfaces to dewarp the acquired image, as disclosed in the present application. If the angle was placed near the middle or upper portion of the image, the extent of either or both of the anterior or posterior corneal surfaces is likely to be insufficient for de-warping purposes.

Figure 14:
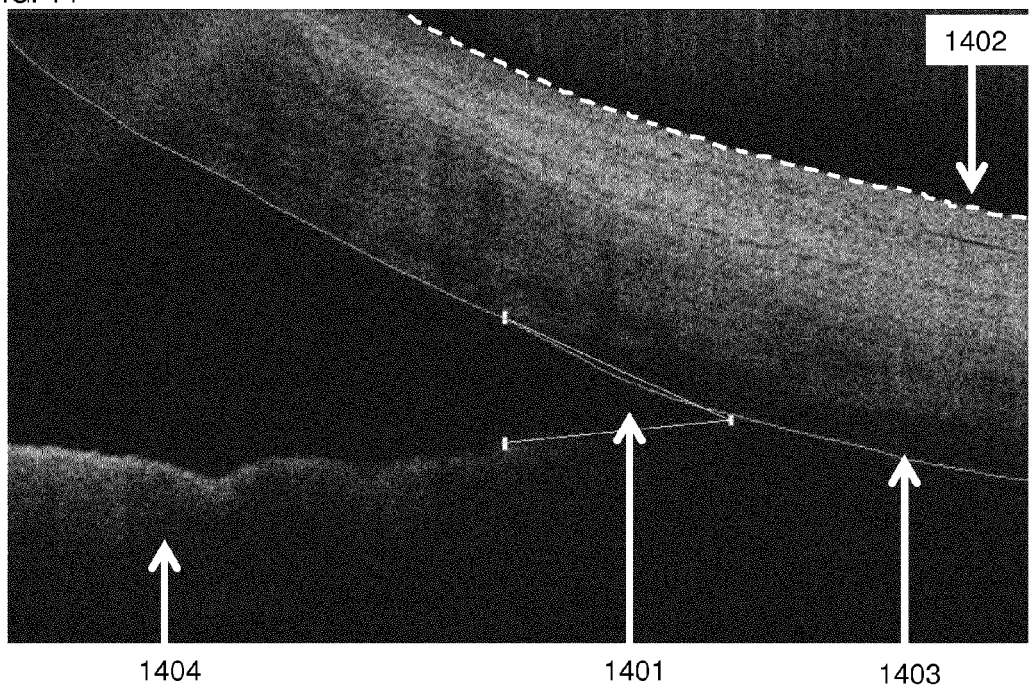
FIG. 14 is a magnified undewarped image of FIG. 13 displaying one meridian of the cornea and is magnified to show the iridocorneal angle (1401). The image has not been dewarped and thus the curvature of the cornea appears inverted to what would be expected in the absence of scan geometry and refraction corrections. The dashed-curve (1402) is the result of the segmentation of the anterior corneal surface. The solid curve (1403) is the posterior corneal surface. A portion of the iris (1404) is also present.

FIG. 14 is a magnified region of FIG. 13 about the iridocorneal angle where the anterior surface (1402) is demarcated as is the posterior corneal surface (1403). Also present is the iris (1404). Measuring the angle (1401) in this non-dewarped image leads to 5.5% error which may not be acceptable in assessment of the anterior chamber angle. After beam geometry and refraction correction, this image is partially measureable. The limited measurability is due to the fact that only a portion of the anterior surface is available in the field-of-view. Without additional information of the true shape of the corneal surfaces, the dewarped image does not represent true anatomy of the anterior segment. Thus in this situation, geometric measurements of structures in the anterior segment would be of dubious utility.

Figure 15:
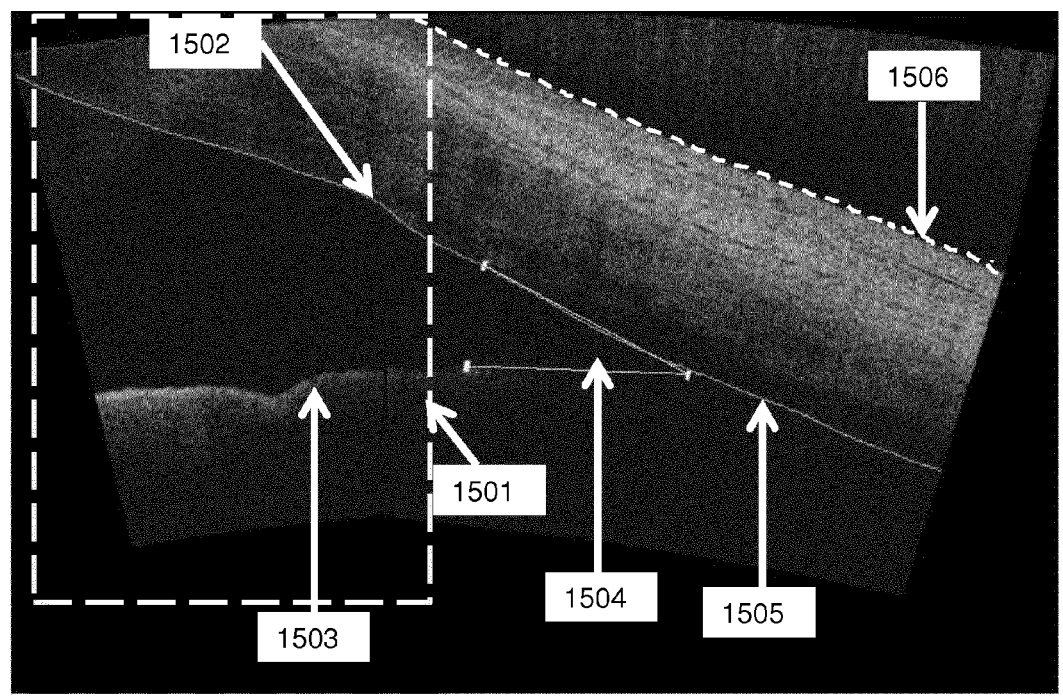
FIG. 15 is a dewarped image of FIG. 14, where the dewarping uses only the corneal surfaces observed in this image. In this partially dewarped image, the dashed-curve (1506) represents the segmentation of the anterior corneal surface; curve 1505 is the segmentation of the posterior corneal surface; location 1504 is the iridocorneal angle. A comparison of this image with its undewarped predecessor (FIG. 14) indicates at least two artifacts: the kink (1502) in the posterior surface and the wrong curvature of the iris (1503) found within the indicated box (1501).

The image in FIG. 15 is a dewarped version of FIG. 14, using information only available in FIG. 14. A comparison of this image with its undewarped predecessor (FIG. 14) reveals at least two artifacts: the kink (1502) in the posterior surface (1505) and the wrong curvature of the iris (1503) found within that box (1501). The anterior corneal surface is designated by the dashed-line (1506). Thus any measurements such as that of the iridocorneal angle (1504) or the determination of geometric metrics under missing segmentation data in this image will result in a less-than-true values.

The measured angle (1401) in the undewarped (FIG. 14) version of this image is 29.22 degrees. After dewarping from a method of the present application (FIG. 15), using both anterior and posterior surfaces, the angle (1504) is measured to be 30.91 degrees.

Figure 16:
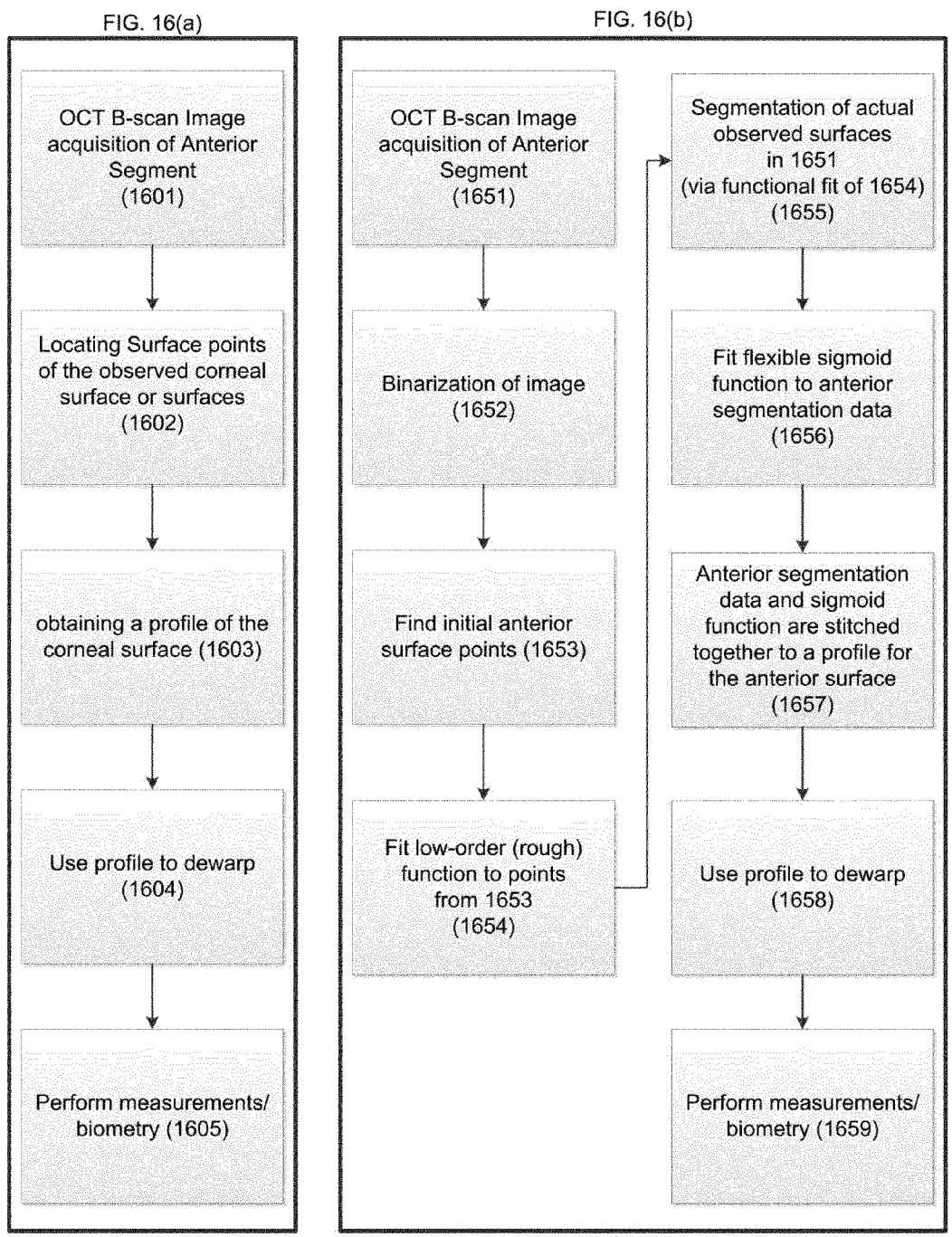
FIG. 16 represents two embodiments of the dewarping method.

In order to overcome the aforementioned problems such as reducing or eliminating artifacts associated with standard dewarping, two embodiments are outlined in FIG. 16. The generalized approach of the dewarping methods outlined in the present application is to accomplish more realistic dewarping given a limited field-of-view of corneal surfaces by constraining, fitting or determining an extended profile of the corneal surface, including both the detected or observed and missing or non-observed surface portions or fragments.

A basic embodiment of this dewarping approach is presented in FIG. 16(a). In this procedure, an OCT image is obtained of the anterior segment (1601). The image data should contain one or more imaged portions of at least one corneal surface. Points are located (1602) on one or more observed portions of the desired surface or surfaces detected in the image. With these points, an extended profile of the corneal surface, including both the detected or observed and missing or non-observed surface portions or fragments, can be constrained, fitted, or determined (1603). After the fit, the image can then be dewarped (1604) using the extended profile, and any desired measurements performed (1605).

Figure 17:
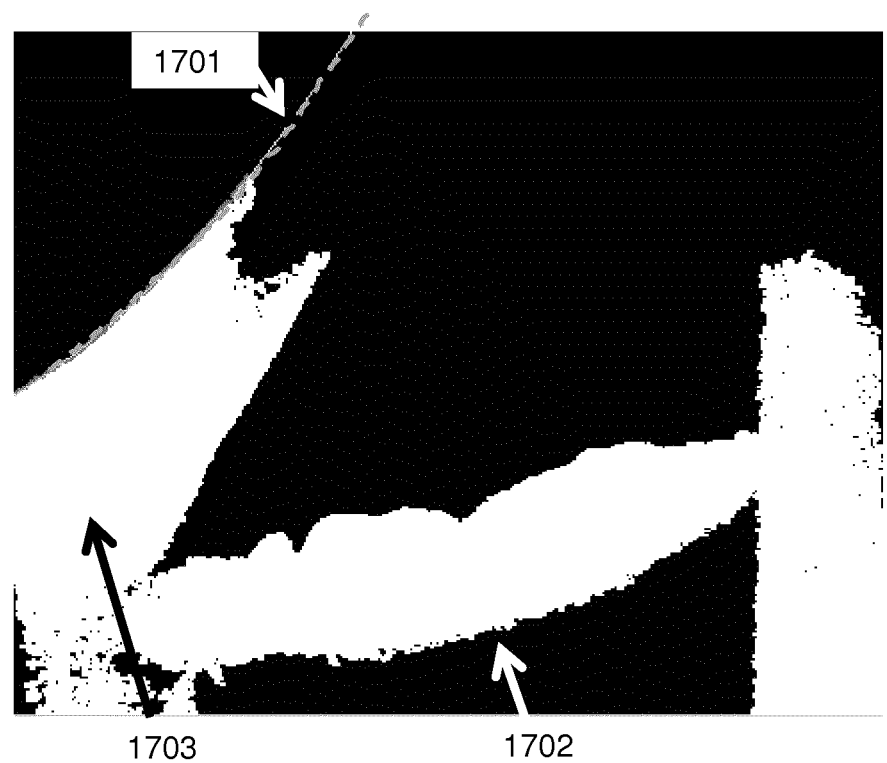
FIG. 17 is a binarized/thresholded image of a limited field-of-view image showing the detected initial corneal anterior surface and a fit to the surface points (1701) thereto. This curve (1701) has been derived from a rough fit to the identified surface points. The structures present include a portion of the cornea (1703) and the iris (1702).

In an exemplary embodiment shown in FIG. 16(b), one or more B-scans (1651) of the anterior segment of an eye are obtained, and are pre-processed using standard techniques. The B-scan image may or may not be of sufficient width to contain both diagonally opposite sides of the cornea. For the moment, the more limiting case is assumed, that only one side has been imaged. Image pre-processing steps can include, for example, co-addition of images taken at or very near a given location, with the option of smoothing in one or both dimensions. The B-scan image is then binarized (1652) as shown in FIG. 17. In FIG. 17, the cornea (1703), the iris (1702), and the rough fit (1701) to the detected surface points are identified. Descriptions of this operation, and others mentioned in this application, may be found in standard texts on image processing (Russ 2011). The binarized image is then divided into subimages, where, in the present case of FIG. 17, the important subimage is the one that contains the anterior corneal surface. The segregation into subimages allows a more automatic approach to targeting the correct or desired surface.

The next step (1653) of the method is to locate the initial anterior corneal surface points in the OCT image in FIG. 17 (1701). A rough fit (1654) is determined from the initial anterior corneal surface points for isolating a portion of that image that contains the corneal anterior surface. To locate the actual points, a graph-based segmentation can be used to determine the location of the points that have been identified based on the rough fit. In order to be able to dewarp the entire image, the depth of the image (axial direction) is extended. As the anterior corneal surface is partially captured in the original image field-of-view, extrapolation of the corneal anterior surface is required to create a surface for the entire field-of-view.

The segmented surface points determined in step 1655 along with a priori information about the corneal surface can be used to accurately determine an extended profile of the corneal surface. For instance, the corneal surface profile or model and curvature information can be extracted from existing central corneal scans of the same subject. This information can help to constrain and construct an extrapolating function.

A profile that is used in the preferred embodiment is to fit a flexible sigmoid function (1656) to the segmentation data available in the image. This can be considered as an extrapolation profile or model of the corneal surface, to the anterior segmentation data in the physical domain according to:

$$f(x) = A + \frac{K-A}{(1+Qe^{-B(x-M)})^{1/v}}.$$

The parameters of this function are constrained using prior knowledge about the extended corneal surface profile or model, if either one is available.

After the fit, the anterior segmentation data and the fit are combined or stitched together (1657) to create a surface that represents the anterior corneal surface. There is the option to smooth the combined profile using B-spline interpolation. The resultant surface can then be used to dewarp (1658) the angle image or other nearby structures. After this step, reliable biometric measurements (1659) can be performed. An exemplary geometric metric is the irido-corneal angle. While the above discussed embodiments emphasized the anterior corneal surface, the method is equally applicable to the posterior surface. The most preferred corneal surface to fit is that of the anterior surface, as it provides the most accurate dewarping. The next most preferred surface is that of the posterior one. A third alternative exists to use both corneal surfaces in the dewarping procedure, as will be discussed in further detail below.

There are other functions that can be used in extrapolations, for example, a quadratic function:

$$ax^2+bxz+cz^2+dx+ez+f=0.$$

The parameters can be constrained to construct the corneal surface for dewarping. Other functional forms can be quadratics, quadrics, conics, sigmoid functions, aspherics (Forbes 2007), higher-order polynomicals, and Zernike or Jacobi polynomials.

Figure 18:
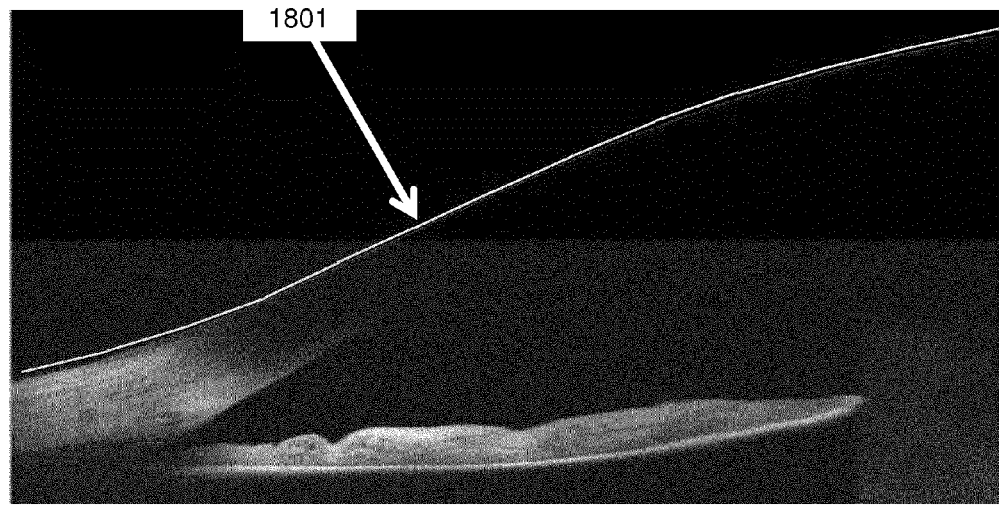
FIG. 18 is an OCT B-scan image that has not been dewarped. In this particular image, the anterior surface is indicated by the extrapolated surface profile (1801), created by stitching the segmentation data and a sigmoid fit of the missing portion of the corneal surface.
Figure 19:
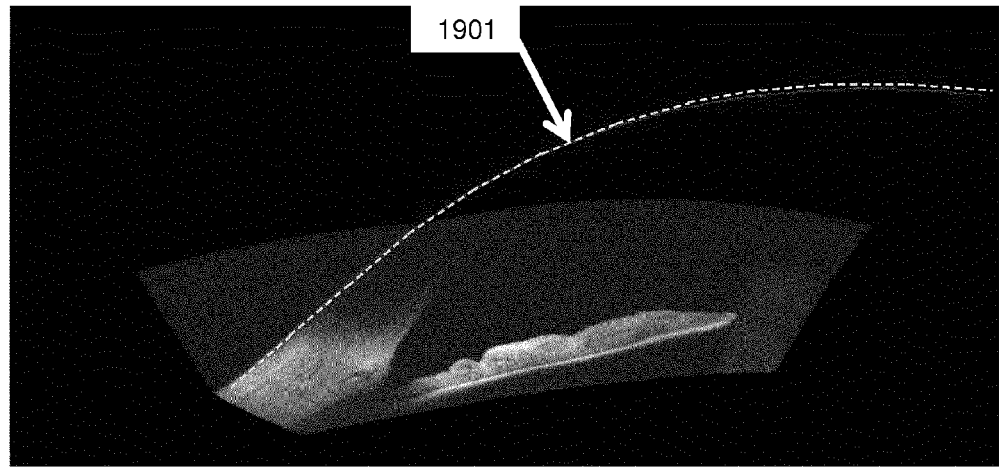
FIG. 19 is a dewarped version of FIG. 18. The curve (1901) was created by stitching the segmentation data and sigmoid fit together, as in FIG. 18. This curve 1901 is the dewarped version of curve 1801.
Figure 20:
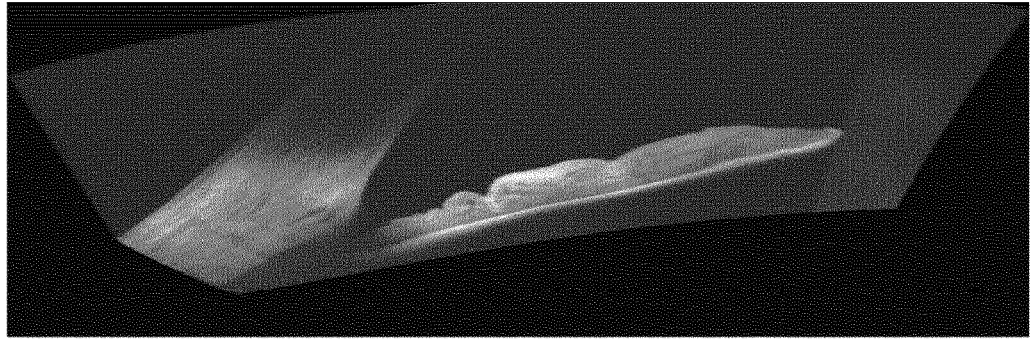
FIG. 20 is an OCT B-scan image is a subimage of image FIG. 19.

The image depicted in FIG. 18 shows an anterior surface reconstruction (1801) without the image having been dewarped. After dewarping, the modified image is given in FIG. 19, with the same profile (1901) of the anterior surface. FIG. 20 is a magnified subimage of that presented in FIG. 19. The same general method can be used for posterior surface re-construction.

Figure 21A:
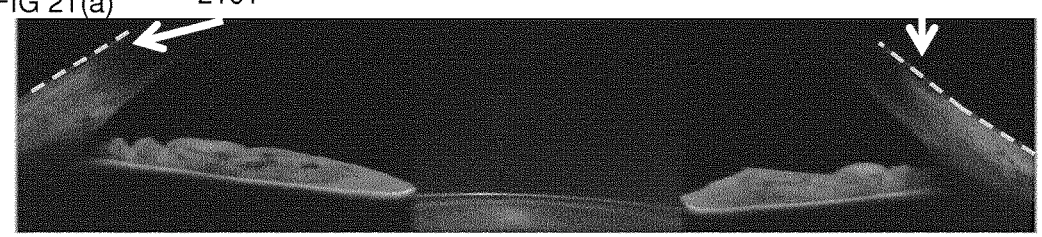
FIG. 21(a) shows the segmentation (2101)
Figure 21B:
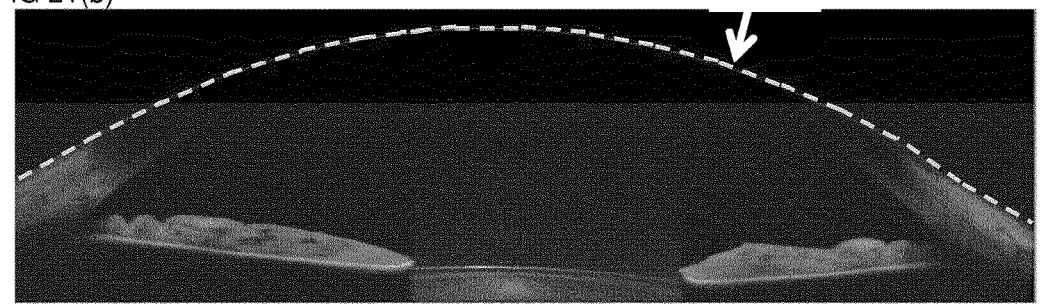
FIG. 21(b) shows the extended anterior corneal surface created with the combined data of segmentation and extrapolating function represented by the curve 2102.
Figure 22:
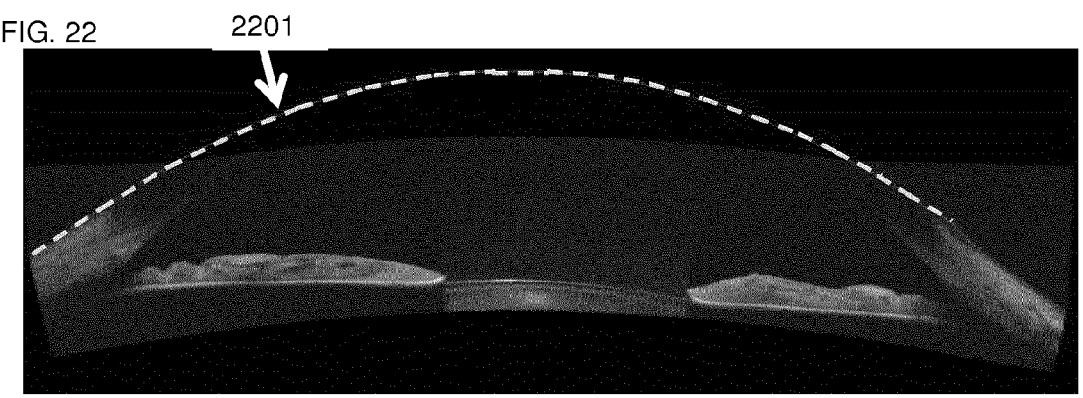
FIG. 22 is a dewarped version of FIG. 21, in which both sides of the anterior corneal surface have been corrected and any measurement of structures within the anterior segment will be more accurate than similar measurements obtained with an undewarped image. The final extended profile (2201) of the anterior corneal surface is also shown.
Figure 23:
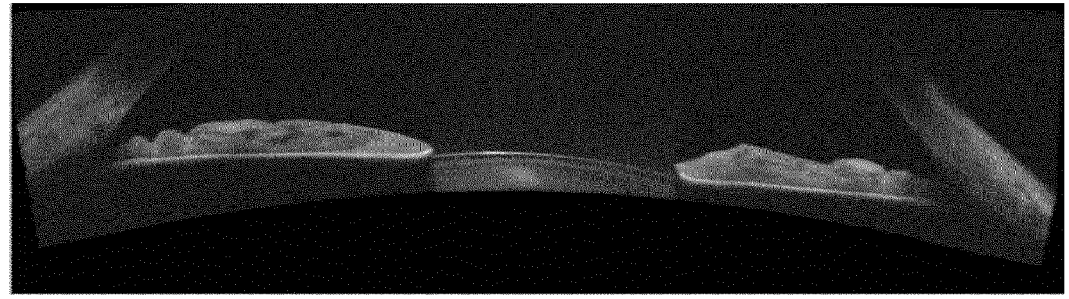
FIG. 23 is a subimage of FIG. 22.

In the case with wide-angle anterior segment imaging, where the image possesses diagonally opposite irido-corneal angles, a similar processing technique is also applicable. FIG. 21(a) shows an image where the vertical or axial extent is limited and part of the corneal anterior surface is not detected. The same procedure as outlined above for one side can be applied in this case, but with the additional information of combining or stitching together three segments: one for each of the corneal surfaces (2101) observed, and the surface profile or model for the region in between. FIG. 21(b) is the same corneal image as in 21(a), but with the full or extended profile (2102) displayed. FIG. 22 is the dewarped version of FIG. 21(b), with the corneal profile (2102) of FIG. 21(b) reproduced as (2201). FIG. 23 is a subimage of FIG. 22. The extrapolation function used in this case could be a quadratic as it is 2D data or quadric in the case of 3D data.

Dewarping using both corneal surfaces can proceed by two different methods. In the first method, a sequential approach, the image is first dewarped using the anterior surface and everything below that surface is dewarped, including the posterior surface. The next step is then to use the dewarped posterior surface, to perform a second dewarping of the image found below that posterior surface. The same algorithm can be used for each of these two dewarpings, but only the input (i.e., which corneal surface) to the algorithm changes.

The second method is to dewarp, point-by-point, using a ray-trace approach, correcting each ray for the refractive properties of the cornea and its surfaces. This second method is rather time consuming and is one that is usually not adopted.

It should be noted that in order to achieve proper dewarping, segmentation of the layer interfaces is imperative. Additional information regarding segmentation and dewarping techniques may be found in US2013208240.

Accurate dewarping can permit additional geometric measurements or metrics to be performed reliably. These include geometric metrics associated with the anterior chamber, such as width, volume, area, and diameter (Radhakrishnan & Yarovoy 2014; Nongpiur et al. 2010; Narayanaswamy et al. 2011; Wu et al. 2011). Geometric metrics associated with the iris include: area, thickness, curvature, and volume (Quigley 2009). Also measureable is the lens vault, which is defined as the perpendicular distance between the anterior pole of the lens and the horizontal line connecting the two scleral spurs (Nongpiur et al. 2011).

Tracking Applications Using Anterior Segment Structures

Tracking of eye movements is often accomplished by using a secondary (often non-OCT) imaging modality based upon a reference feature, structure, or mark seen within the eye. When imaging the retina, reference marks can be such anatomical features as the optical nerve head, blood vessels, or the fovea. When imaging the anterior segment, and in particular, when there is limited field-of-view of the structures within the anterior segment, the iridocorneal angle provides a well-defined geometric structure that can be used as a reference mark. Another geometric structure that could be used as a reference mark is the rear surface of the iris. In this embodiment, OCT images can be acquired and aligned in such a way that the iridocorneal angle can be captured with desired coordinates in the image domain. This is important for the following reasons: visibility of other geometric structures in the anterior segment; an efficient workflow; and accurate measurements. In the case of enhanced depth imaging mode (Spaide et al. 2008; U.S. Pat. No. 8,605,287), it is desired to place the angle close to the zero-delay which is at the bottom of the image. This produces better signal and visibility of structures such as the corneal surfaces which are required for dewarping.

Historically, manual alignment of the delay position is time consuming and may not be successful with a limited field-of-view. The smallest eye motion in axial/longitudinal or lateral directions can easily move the angle from the desired location. Thus a real-time or fast automatic method to track and align is desirable. Plus with the implementation of tracking/accurate aligning in the anterior segment, precise positioning control of the placement of ROIs within an image becomes viable.

Figure 24:
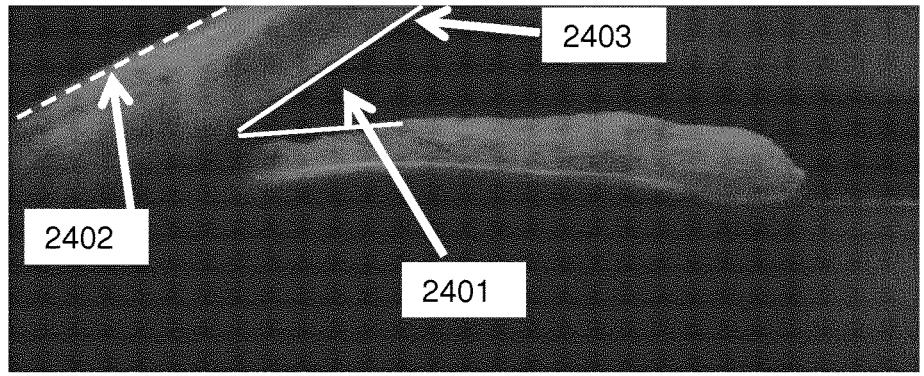
FIG. 24 is a sub-optimal field-of-view B-scan of the a portion of the anterior segment including the iridocorneal angle (2401). The anterior (2402) and posterior (2403) corneal surfaces are indicated.
Figure 25:
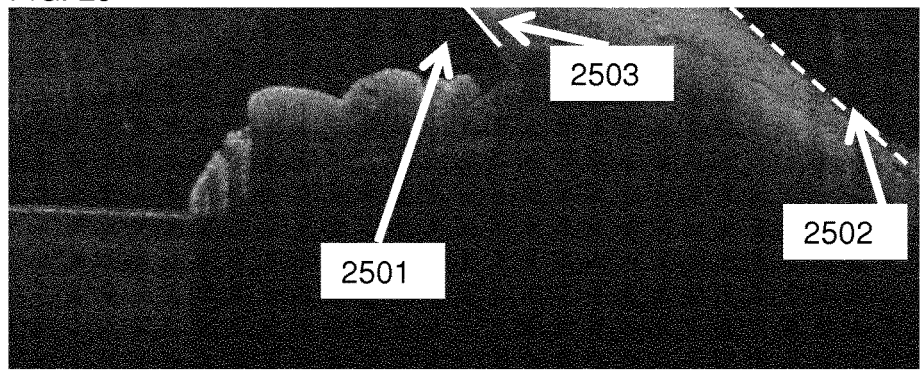
FIG. 25 is another example, like that of FIG. 24, which shows poor placement of the structures of the anterior segment. The iridocorneal angle (2501), the anterior (2502) and posterior (2503) corneal surfaces are indicated.

FIGS. 24 and 25 are two images which show that the iridocorneal angle (2401 and 2501, respectively) is far from being in a useful position. The small segments of the anterior (2402 and 2502) and posterior (2403 and 2503) corneal surfaces so captured are inadequate for dewarping purposes. The axial position of the iridocorneal angle in both images is also unfortunate, as it is far from the zero-delay position should enhanced depth imaging be used.

FIGS. 26 and 27 are two optimally-taken images which show the angle has been placed in a good position. In each of these figures, the iridocorneal angle is indicated (2601 and 2701). FIG. 26 shows larger segments of the anterior (2602) and posterior (2603) surfaces which can permit more accurate dewarping. In order to implement a procedure that is appropriate for real-time tracking and alignment, the main criterion is that the procedure be computationally light. The procedure is to estimate the approximate center position of the angle which is essentially the intersection of the posterior surface with the anterior iris surface by minimizing the watershed function of the distance-transform image. This image is computed based on the binarized image of the angle image. The approach has few steps and avoids angle segmentation or complicated analysis of the image.

FIG. 28 shows a well-aligned B-scan containing the iridocorneal angle (2801). Applying binarization/thresholding to this image yields FIG. 29 and the iridocorneal angle (2901) remains well recognizable. This binary image will then have two connected components: one associated with the cornea (2902) and the other with that of the iris (2903). The Euclidean distance-transform of the binary image is computed, shown in FIG. 30, and the watershed line (the connectivity of local maxima) between two catchment basins (cornea and iris) is computed and is overlaid on this image (3001). The (x,y) image coordinates of the watershed line that minimizes the watershed function $f(x,y)$ is the angle position:

$$\min f(x,y), x \in [1,w], y \in [1,h],$$

where w and h are the image width and height, respectively. FIG. 31 shows the watershed function $f$ vs y axis only, and is based upon processing the image in FIG. 28.

In FIG. 32, which is the same image as that of FIG. 28, the watershed line is shown (3202). This represents the boundary, in this particular case, between two image regions: the iris and the cornea. While the watershed functions in FIGS. 30-32 are plotted as a function of y, the other possibility is using x as the independent variable. In FIG. 32 the x, y values (3201) for the minimum of the watershed function $f$ (3202) are given.

The execution time of the algorithm can be accelerated by isolating and processing an ROI (see 3301 in FIG. 33(a)), ideally around the tail of the connected component associated with the iris as show in FIG. 33(a). This ROI, is then processed as disclosed above, to yield a watershed function indicated in FIG. 33(c) as the black line (3302) on the distance-transform image. The distance transform image with the greater field-of-view, FIG. 30, has the full extent of the watershed line (3001) indicated. The watershed function for FIG. 33(c) is given in FIG. 34.

An alternative approach to that disclosed hereinabove, is to use a template for the iridocorneal angle within a matching or cross-correlation method. Once the angle position for a given image has been detected, an ROI centered at that angle position can be extracted from the input image as a template. This template will then be input to a template matching for the subsequently obtained images. The template can be updated during alignment and/or tracking using the current (or present) image. The template matching function that is maximized could be a 2-D normalized cross-correlation function or similar, as would be readily recognized by the ordinary skilled person in the art. Although various applications and embodiments that incorporate the teachings of the present application have been shown and described in detail herein, those skilled in the art can readily devise other varied embodiments that still incorporate these teachings.

REFERENCES

Patent Literature

US20130208240
US20130188140
US20130208240
US20120249956
US20120271288
U.S. Pat. No. 8,414,564

U.S. Pat. No. 7,884,945
U.S. Pat. No. 8,605,287
WO2014021782

Non-Patent Literature

Canny 1986, IEEE Trans Patt Anal Mach Intell, PAMI-8(6), 679-98.
Fischler & Bolles 1981, Comm ACM 24(6), 381-95.
Hofer et al. 2002, Opt Expr 18(5), 4898-919.
Westphal et al. 2002, Opt Expr 20(9), 397-404.
Wojtkowski et al. 2002, Opt Lett 27(16), 1415-17.
Zhang et al. 2005, Opt Lett 30(2), 147-49.
Kovesi 2003, Proc. DICTA, 309-318.
Zhang et al. 2004, Opt Exp 12, 6033-6039.
Van Herick et al. 1969, Am J Ophthal 68, 626-629.
Smith 1979, Br J Ophthal 63, 215-220.
Friedman & He 2008, Surv Ophthal 53, 250-273.
Westphal et al. 2002, Opt Exp 10, 397-404.
Ishikawa & Schuman 2004, Ophthal Clin North Am 7, 7-20.
Kai-shun et al. 2008, Invest Ophthal Vis Sci 49, 3469-3474.
Wirbelauer et al. 2005, Arch Ophthal 123, 179-185.
Ortiz et al. 2010, Opt Exp 18, 2782-2796.
Ortiz et al. 2009, App Opt 48, 6708-6715.
Radhakrishnan et al. 2007, Invest Ophthal Vis Sci, 48, 3683-3688.
Wu et al. 2011, Arch Ophthalmol. 129(5), 569-574.
Narayanaswamy et al. 2011, Arch Ophthalmol. 129(4), 429-434.
Nongpiur et al. 2010, Ophthalmol. 117, 1967-1973.
Radhakrishnan & Yarovoy 2014, Curr Opin in Ophthal 25, 98-103.
Quigley 2009, Am J Ophthalmol 148, 657-669.
Quigley et al. 2009, J Glaucoma 18, 173-179.
Spaide et al. 2008, Am J Ophthalmol 146, 496-500.
Forbes 2007, Opt Exp 15, 5218-5226.
Wang 2007, App Phys Lett 90, 054103
Baumann et al. 2007, Opt. Expr 15, 13375-13387
Maurer et al. 2003, IEEE Trans Patt Anal Mach Intell 25, 265-270.
Rosenfeld & Pfaltz 1966, J Ass Comp Mach 13, 471-494.
Paglieroni 1992, Comp Vis Graph Image Proc 54, 57-58.
Meyer 1994, Sig Proc 38, 113-125.

Books

Parker 1997, *Algorithms for Image Processing and Computer Vision*, Wiley: New York, ISBN: 047114056-2.
Umbaugh 2010, *Digital Image Processing and Analysis*, $2^{nd}$ Edition, ISBN: 978-1439802052, CRC Press.
Rucklidge, W. 1996, Ph.D. thesis, in *Lecture Notes in Computer Science* (Book 1173), ISBN 9783540619932, Springer Verlag.
Russ 2011, *The Image Processing Handbook*, $6^{th}$ edition, ISBN:978-1439840450.

The invention claimed is:

1. A method to dewarp image data of the anterior segment of an eye collected using an optical coherence tomographic instrument (OCT), said image data containing one or more observed fragments of one or more corneal surfaces, said method comprising:
processing said image data to locate one or more observed fragments of a first corneal surface;
determining an extended profile of said first corneal surface using the observed fragments of the first corneal surface and information related to the first corneal surface not contained in the image data;
dewarping the image data based upon the determined extended profile of the first corneal surface; and,
displaying to a user or storing the dewarped image data.

2. The method as recited in claim 1, further comprising:
repeating the processing and determining steps for a second corneal surface, in which an extended profile for the second corneal surface is determined; and,
using the extended profiles of both said first and second corneal surfaces to dewarp the image.

3. The method as recited in claim 1, in which the first corneal surface is either the anterior corneal surface or the posterior corneal surface.

4. The method as recited in claim 1, in which the processing step includes segmentation to locate said observed fragments; and,
using the results of the segmentation to determine the extended profile of said first corneal surface.

5. The method as recited in claim 1, in which the extended profile for the first corneal surface is chosen from the group consisting of: quadratics, quadrics, higher-order polynomials, sigmoid functions, Zernike polynomials, conics, Jacobi polynomials, and aspherics.

6. The method as recited in claim 1, wherein the information related to the first corneal surface not contained in the image data that is used to create the extended profile is based on additional images of the cornea.

7. The method as recited in claim 1, in which the extended profile is determined by extrapolating information of the first corneal surface contained in said image data.

8. The method as recited in claim 1, wherein the information related to the first corneal surface not contained in the image data that is used to create the extended profile is based on a model of the first corneal surface.

9. The method as recited in claim 1, in which the method is automatically executed.

10. The method as recited in claim 1, further comprising:
determining one or more geometric metrics from the dewarped image; and,
reporting and/or storing said metrics.

11. The method as recited in claim 10, in which geometric metrics can be the length or diameter, angles, area, volume, thickness, or curvature of structures found within the anterior segment.

12. An optical coherence tomographic (OCT) system for imaging of an eye of a patient comprising:
a light source for generating a beam of radiation;
a beam divider for separating the beam of radiation into a sample arm and a reference arm;
optics for scanning the beam in the sample arm transversely over the eye;
a detector for measuring light radiation returning from the eye and reference arm and for generating output signals in response thereto; and,
a processor for generating image data based on the output signals, said image data containing one or more observed portions of a corneal surface,
said processor functions also to dewarp a portion of the image data, in which dewarping is performed based upon an extended profile of the corneal surface determined by using one or more observed portions of said corneal surface and information related to the corneal surface not contained in the image data.

13. The OCT system as recited in claim 12, wherein said processor functions also to determine one or more geometric metrics; and,
stores and/or reports to a user said one or more geometric metrics.

14. The OCT system as recited in claim 12 in which the processor for generating an image and the processor for dewarping are distinct.

15. The OCT system as recited in claim 14, in which at least one of the processors is a parallel processor.

16. The OCT system as recited in claim 12 wherein the information related to the corneal surface not contained in the image data used to derive the extended profile is based on additional images of the cornea.

17. The OCT system as recited in claim 12 wherein the information related to the corneal surface not contained in the image data used to derive the extended profile is based on a model of the corneal surface.

18. A method to adjust automatically an optical coherence tomographic (OCT) system to optimize the locations of structures found in the anterior segment of an eye of a patient, said OCT system having a sample arm and a reference arm, the relative positions thereof defining a delay position, comprising:
   obtaining OCT image data at an initial delay position;
   processing said OCT image data to identify a set of structures detected therein;
   ascertaining the location of one or more corneal surfaces using one or more structures in the set;
   identifying an amount of overlap of the one or more corneal surfaces with other structures in the set; and,
   adjusting the delay position to reduce the amount of overlap in said OCT image data.

19. The method as recited in claim 18, in which the amount of overlap is determined by statistical metrics.

20. The method as recited in claim 18, in which the amount of overlap is determined by statistical analyses of a watershed line by one or more connectivity metrics.

21. The method as recited in claim 18, in which the B-scan contains data on both sides of the zero-delay position.

22. The method as recited in claim 18, in which the structures include corneal anterior and posterior surfaces and mirror images of the iris and/or the crystalline lens.

23. The method as recited in claim 18, in which the adjustment of the OCT system to reduce or eliminate said overlap occurs in real-time.

* * * * *

UNITED STATES PATENT AND TRADEMARK OFFICE
CERTIFICATE OF CORRECTION

PATENT NO. : 9,833,136 B2
APPLICATION NO. : 15/104447
DATED : December 5, 2017
INVENTOR(S) : Homayoun Bagherinia Page 1 of 1

It is certified that error appears in the above-identified patent and that said Letters Patent is hereby corrected as shown below:

In Column 6, Line 57, delete "the a" and insert -- a --, therefor.

In Column 16, Line 20, after "in" insert -- the --.

In Column 16, Line 27, delete "polynomicals," and insert -- polynomials, --, therefor.

In Column 19, Line 37, after "90, 054103" insert -- . --.

In Column 19, Line 38, after "13375-13387" insert -- . --.

Signed and Sealed this
Twentieth Day of March, 2018

Andrei Iancu
*Director of the United States Patent and Trademark Office*